(12) United States Patent
Myerson et al.

(10) Patent No.: US 7,618,777 B2
(45) Date of Patent: Nov. 17, 2009

(54) COMPOSITION AND METHOD FOR ARRAY HYBRIDIZATION

(75) Inventors: Joel Myerson, Berkeley, CA (US); Michael Barrett, Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 550 days.

(21) Appl. No.: 11/082,476

(22) Filed: Mar. 16, 2005

(65) Prior Publication Data

US 2006/0210997 A1 Sep. 21, 2006

(51) Int. Cl.
*C12Q 1/68* (2006.01)
*C07H 21/00* (2006.01)
*C07H 21/02* (2006.01)

(52) U.S. Cl. .................. 435/6; 536/24.3; 536/24.33

(58) Field of Classification Search ............ 435/6; 536/24.3, 24.33
See application file for complete search history.

(56) References Cited

U.S. PATENT DOCUMENTS

| | | | |
|---|---|---|---|
| 2,826,551 A | 3/1958 | Green | |
| 3,268,593 A | 3/1958 | Green | |
| 2,846,458 A | 8/1958 | Haluska | |
| 3,234,252 A | 2/1966 | Pater | |
| 3,427,271 A | 2/1969 | McKellar | |
| 3,964,500 A | 6/1976 | Drakoff | |
| 4,047,958 A | 9/1977 | Yoneyama et al. | |
| 4,117,249 A | 9/1978 | De Simone et al. | |
| 4,152,416 A | 5/1979 | Spitzer | |
| 4,160,776 A | 7/1979 | Scardera et al. | |
| 4,226,794 A | 10/1980 | Scardera et al. | |
| 4,337,168 A | 6/1982 | Scardera et al. | |
| 4,364,837 A | 12/1982 | Pader | |
| 4,380,451 A | 4/1983 | Steinberger et al. | |
| 4,427,958 A | 1/1984 | Charlesworth et al. | |
| 4,728,457 A | 3/1988 | Fieler et al. | |
| 5,137,765 A | 8/1992 | Farnsworth | |
| 5,156,834 A | 10/1992 | Beckmeyer et al. | |
| 5,266,222 A | 11/1993 | Willis et al. | |
| 5,624,711 A | 4/1997 | Sundberg et al. | |
| 5,639,626 A * | 6/1997 | Kiaei et al. | 435/7.92 |
| 5,650,543 A | 7/1997 | Medina | |
| 5,985,793 A | 11/1999 | Sandbrink et al. | |
| 6,186,659 B1 | 2/2001 | Schembri | |
| 6,313,182 B1 | 11/2001 | Lassila et al. | |
| 6,420,114 B1 * | 7/2002 | Bedilion et al. | 435/6 |
| 6,503,413 B2 | 1/2003 | Uchiyama et al. | |
| 6,543,968 B2 | 4/2003 | Robinson | |
| 2002/0011584 A1 | 1/2002 | Uchiyama et al. | |
| 2003/0013092 A1 | 1/2003 | Holcomb et al. | |
| 2005/0142563 A1* | 6/2005 | Haddad et al. | 435/6 |

FOREIGN PATENT DOCUMENTS

EP A 0633018 1/1995

(Continued)

OTHER PUBLICATIONS

Product Data Sheet, Tego Wet 206, Substrate wetting additive, Issue date of Jan. 2004, Tego Chemie Service GmbH.

(Continued)

*Primary Examiner*—Jezia Riley

(57) ABSTRACT

The present disclosure relates to a system, composition, and method for hybridizing a microarray. The composition includes a superwetting agent. The method includes contacting the microarray with an aqueous mixture including the superwetting agent.

16 Claims, 1 Drawing Sheet

FOREIGN PATENT DOCUMENTS

Figure 1:
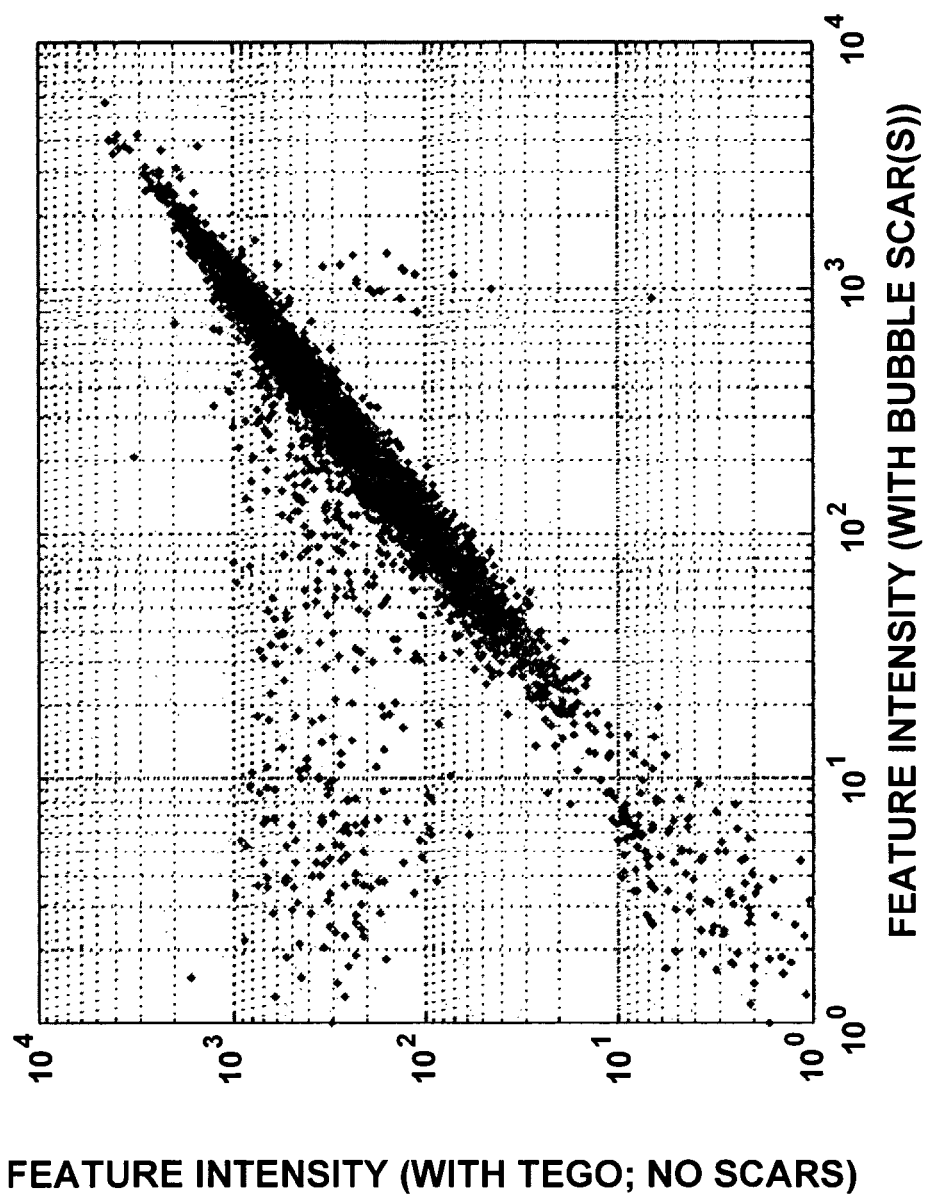

| | | |
|---|---|---|
| EP | 1 186 671 A2 | 3/2002 |
| GB | 849433 | 9/1960 |
| WO | WO03/010338 A | 2/2003 |

OTHER PUBLICATIONS

EnviroGem AE Surfactants Readily Biodegradable, Antifoaming Wetting Agents, Air Products, Air Products and Chemicals, Inc., 2004.

Dynol 604 Surfactant, Air Products, Air Products and Chemicals, Inc., 1998.

Application Information, 3M Novec Fluorosurfactants For Paints and Coatings, Issued Oct. 2003.

A new generation of flurosurfactants, Dr. Michael Terrazas nd Dr. Rudi Dams introduce two new products from 3M, Speciality Chemicals Magazine, Mar. 2004; vol. 24 No. 3.

Masurf FS-Fluorosurfactants-Industrial, Mason Chemical Company, file://C:\IE_Temp\OLK77\Masurf%20%20FS-Fluorosurfactants1. htm, Copyright 2003 Mason Chemical Company, pp. 1-3.

Novel Fluorinated Materials Replace Long Chain Surfactants, Dr. Barry Rosenbaum/Omnova Solutions, Inc., Posted on May 31, 2002.

Agilent 60-mer oligo microarray processing protocol, Part No. G4140-90030, Apr. 2004, Version 4.1.

Agilent 60-mer oligo microarray procesing protocol, Part No. F4140-90050, Version 2.1, Apr. 2004.

Array-Based CGH Procedures for Genomic DNA Analysis, Version 1.00, Jan. 2005, Part No. G4410-90010.

Nimblegen Chip Protocol optimized by Christopher Wong, GIS, NimbleGen Systems, Inc. and A Star Genome Institute of Singapore, Christopher Wong, Aug. 2003; pp. 1-4.

Bauer Center for Genomics Research, Preparation of Affymetrix GeneChips and Target Hybridization Cocktail, Jennifer A. Couget, Aug. 26, 2003; pp. 1-4.

Array Hybridization Procedures, A Concise Guide to cDNA Microarray Anaylsis, Priti Hegde, Rong Qi, Kristie Abernathy, Cheryl Gay, Sonia Dharap, Renee Gaspard, Julie Earle-Hughes, Erik Snesrud, Norman Lee, and John Quackenbush, The Institute for Genomic Research, Rockville, MD 20850.

DuPont Zonyl Fluoroadditives, Technical Information, Dupont Chemical Solutions Enterprise, Copyright 2002 E.I. du Pont de Nemours and Company.

3M Novec Fluorosurfactant FC-4432, Product Information, 3M Performance Materials Division, Issued Oct. 2003.

3M Novec Fluorosurfactant FC-4430, Product Information, 3M Performance Materials Division, Issued Oct. 2003.

Laying the Foundation for New Technologies, 3M creates a new building block for its fluorosurfactants, Darlene Brezinski, Reprinted with permission from the Jan. 2003 issue of Paint & Coatings Industry Magazine.

EnviroGem AD01 Surfactant Defoaming Wetting Agent, Air Products, Air Products and Chemicals, Inc., 2002.

Partial European Search Report EP06251406 dated May 23, 2006.

* cited by examiner

COMPOSITION AND METHOD FOR ARRAY HYBRIDIZATION

BACKGROUND

Microarrays of DNA or RNA polynucleotides or oligonucleotides are state-of-the-art biological tools used in the investigation and evaluation of genes for analytical, diagnostic, and therapeutic purposes. Microarrays typically comprise a plurality of oligomers, synthesized or deposited on a glass support or substrate in an array pattern. The support-bound oligomers are called "probes", which function to bind or hybridize with a sample of DNA or RNA material under test, called a "target" in hybridization experiments. Some investigators also use the reverse definition, referring to the surface-bound oligonucleotides as targets and the solution sample of nucleic acids as probes. Further, some investigators bind the target sample under test to the microarray substrate and put the oligomer probes in solution for hybridization. Either of the "target" or "probes" may be the one that is to be evaluated by the other. Thus, either one could be an unknown mixture of polynucleotides to be evaluated by binding with the other. All of these iterations are within the scope of the present disclosure. In use, the array surface is contacted with one or more targets under conditions that promote specific, high-affinity binding of the target to one or more of the probes. The targets are typically labeled with an optically detectable label, such as a fluorescent tag, so that the hybridized targets and probes are detectable with scanning equipment. DNA array technology offers the potential of using a multitude (e.g., hundreds of thousands) of different oligonucleotides to analyze changing mRNA populations.

Hybridization of DNA microarrays typically employs a target solution having a suitable buffer. Such buffers often include anionic detergents such as sodium dodecyl sulfate, lithium lauryl sulfate, N-lauryl sarcoside, or non-ionic detergents such as Tween 20® or Triton X-102®. Known hybridization buffers provide at least some wetting and flow characteristics. Wetting and flow characteristics of the buffer, the target solution, or combinations thereof, can be significant when, for example, the DNA microarray slides that are used are hydrophobic. Appropriate flow characteristics can also be advantageous when, for example, it is desirable to use mixing or agitation to help distribute the target solution uniformly over the entire array surface over time. Such mixing can influence the hybridization kinetics and thermodynamics.

One way uniform mixing can be accomplished is by incorporating a bubble in the hybridization chamber along with the buffered target solution. Rotation of the hybridization chamber causes the bubble to move around the perimeter of the chamber, and aids in mixing the bulk solution. Due to the hydrophobic nature of some DNA microarray slides, their resistance to being wetted, their tendency to become dewetted once wet, and other factors, movement of this bubble can be problematic. For example, bubbles can form on the surface of the slide that are resistant to movement that can result in non-uniform exposure of the array to the target solution. In some instances "bubble scars" or defects can be observed where hybridization occurs very poorly or not at all due to non-uniform exposure of the array to the target solution. Other hybridization methods involving mixing do not use bubbles. However, appropriate flow and wetting characteristics can play a significant role in these methods as well.

The problem of sporadic or poor hybridization assay performance can be characterized by, for example, low-intensity or missing features on the microarray substrate, high backgrounds, and visually "blotchy" substrates. This problem can be observed using conventional hybridization conditions at hybridization temperatures of, for example, about 66° C. and a hybridization time of about 14 to 18 hours. The poor performance characteristics can be observed in as little as 6 hours of incubation time at high temperature in conventional buffer solutions.

Thus, there remains a need for materials, conditions and methods for hybridizing surfaces, such as DNA microarrays on siliceous substrates, that have improved hybridization assay performance and uniformity.

SUMMARY

In general terms, the disclosure relates to a system, composition, and method for associating molecules with a surface, for example, hybridizing a first oligonucleotide bound to a surface with a second unbound oligonucleotide.

One possible aspect of the disclosure is a method of hybridizing a first oligonucleotide bound to a surface with a second unbound oligonucleotide, comprising: contacting the surface with an aqueous mixture comprising a superwetting agent.

Another possible aspect of the disclosure is a buffer concentrate comprising: a superwetting agent and a buffer.

Still another possible aspect of the disclosure is a product of mixing comprising: a superwetting agent; an organosulfate surfactant or salt thereof; a water soluble organosulfonic acid or salt thereof; an organopolyalkoxylate; a chelator or salt thereof; a source of a monovalent cation; and optionally an aqueous carrier.

Yet another possible aspect of the disclosure is a kit for hybridizing an oligonucleotide material comprising: a buffer concentrate comprising a superwetting agent; an optional microarray having a siliceous substrate, wherein a surface of the substrate is optionally derivatized, and optionally having a plurality of oligonucleotides attached to the surface in an array pattern of features; and instructions for using the buffer concentrate to hybridize the oligonucleotide attached to a microarray.

BRIEF DESCRIPTION OF THE DRAWINGS(S)

FIG. 1 shows a comparative scatter plot of observed feature intensity for two arrays, one with scar defects and without scar defects, in embodiments of the present disclosure.

DETAILED DESCRIPTION

Various embodiments of the present disclosure will be described in detail with reference to drawings, if any. Reference to various embodiments does not limit the scope of the disclosure, which is limited only by the scope of the claims attached hereto. Additionally, any examples set forth in this specification are not intended to be limiting and merely set forth some of the many possible embodiments for the claimed invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present disclosure, the preferred methods and materials are now described. Methods recited herein may be carried out in any order that is logically possible, in addition to a particular order disclosed.

All publications mentioned herein are incorporated herein by reference to disclose and describe the methods and materials in connection with which the publications are cited. The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

The practice of the present disclosure will employ, unless otherwise indicated, conventional techniques of chemistry, biochemistry, molecular biology, and medicine, including diagnostics, which are within the skill of the art. Such techniques are explained fully in the literature.

The following definitions are provided for specific terms that are used in the following written description.

Definitions

The following terms are intended to have the following general meanings as they are used herein.

"Superwetting agent" refers to a compound or composition that has an ability to significantly enhance the distribution of the compound, the composition, or other formulation constituents, particularly target or probe compositions, onto and across a surface. "Surface" generally refers to the exterior boundary of an object or body, for example, a porous or non-porous solid or substrate, a liquid, a gas such as a bubble, and combinations thereof, such as a composite, foam, gel, and like formulations, and can include an interface between or within like or dissimilar materials. Thus, for example, a suitable wetting liquid will spread on a surface that has been treated with a suitable superwetting agent, for example, an array-liquid interface, an array-bubble interface, an array-superwetting agent interface, a superwetted array-liquid interface, an liquid-gas interface, a superwetted gas-liquid interface, and like surfaces or interfaces. A superwetted surface prevents, for example, a solid surface from being repellent to a wetting liquid. Superwetting agents of the present disclosure provide surface-wetting and surface tension lowering that are greater than compared to conventional wetting agents. A superwetting agent in the buffer formulations of the present disclosure can significantly lower the equilibrium (static) surface tension, dynamic surface tension, or both, of the resulting contacted surface. Thus, superwetting agents useful in the practice of the present disclosure can be identified and selected based on, for example, empirical or known chemical compatibilities, stabilities, surface tension properties, and like properties. Suitable superwetting agents can provide surface tensions of, for example, less than about 75 mN/m at 25° C. at a 0.1 weight percent concentration in water. Other suitable superwetting agents can provide surface tensions of, for example, less than about 65 mN/m at 25° C. at a 0.1 weight percent concentration in water. Still other suitable superwetting agents can provide surface tensions of, for example, less than about 55 mN/m at 25° C. at a 0.1 weight percent concentration in water. Yet still other suitable superwetting agents can provide surface tensions of, for example, less than about 45 mN/m at 25° C. at a 0.1 weight percent concentration in water. Still other suitable superwetting agents can provide surface tensions of, for example, less than about 35 mN/m at 25° C. at a 0.1 weight percent concentration in water. Yet still other suitable superwetting agents can provide surface tensions of, for example, less than about 25 mN/m at 25° C. at a 0.1 weight percent concentration in water. Yet still other suitable superwetting agents can provide surface tensions of, for example, less than about 20 mN/m at 25° C. at a 0.1 weight percent concentration in water. Generally, the lower the surface tension of a surface that has been contacted by a superwetting agent formulation of the present disclosure will produce superior hybridization results and performance reliability. Superwetting agents are known and are commercially available, as described herein. Surface-tension and interfacial-tension measurement methods and techniques are known to those skilled in the art.

"Surfactant" refers generally to any surface-active substance, such as detergent.

"Water soluble" refers to the dispersibility property of a substance in water and includes, for example, molecular dispersibility of the substance, particulate dispersibility of the substance in water, or both, at one or more temperatures.

"Mixture" refers to, for example, an aqueous solution, a dispersion, or a biphasic or multiphasic combination of disclosed ingredients or components, such as a superwetting agent, and other components of the buffered compositions. The buffer composition or mixtures of the present disclosure mixture are preferably aqueous solutions or dispersions.

"Nucleic acid" refers to a high molecular weight material that is a polynucleotide or an oligonucleotide of DNA or RNA.

"Polynucleotide" refers to a compound or composition that is a polymeric nucleotide or nucleic acid polymer. The polynucleotide may be a natural compound or a synthetic compound. In the context of an assay, the polynucleotide can have from about 20 to 5,000,000 or more nucleotides. The larger polynucleotides are generally found in the natural state. In an isolated state the polynucleotide can have about 30 to 50,000 or more nucleotides, usually about 100 to 20,000 nucleotides, more frequently 500 to 10,000 nucleotides. Isolation of a polynucleotide from the natural state can often result in fragmentation. The polynucleotides can include nucleic acids, and fragments thereof, from any source in purified or unpurified form including DNA, double-stranded or single-stranded (dsDNA and ssDNA), and RNA, including t-RNA, m-RNA, r-RNA, mitochondrial DNA and RNA, chloroplast DNA and RNA, DNA/RNA hybrids, or mixtures thereof, genes, chromosomes, plasmids, the genomes of biological materials such as microorganisms, for example, bacteria, yeasts, viruses, viroids, molds, fungi, plants, animals, humans, and like materials. The polynucleotide can be only a minor fraction of a complex mixture such as a biological sample. Also included are genes, such as hemoglobin gene for sickle-cell anemia, cystic fibrosis gene, oncogenes, cDNA, and like genetic materials.

Polynucleotides include analogs of naturally occurring polynucleotides in which one or more nucleotides are modified over naturally occurring nucleotides. Polynucleotides then, include compounds produced synthetically, for example, PNA as described in U.S. Pat. No. 5,948,902 and the references cited therein, all of which are incorporated herein by reference, which can hybridize in a sequence specific manner analogous to that of naturally occurring complementary polynucleotides.

The polynucleotide can be obtained from various biological materials by procedures well known in the art. The polynucleotide, where appropriate, may be cleaved to obtain a fragment that contains a target nucleotide sequence, for example, by shearing or by treatment with a restriction endonuclease or other site-specific chemical cleavage method.

In embodiments, the polynucleotide, or a cleaved fragment obtained from the polynucleotide, can be at least partially denatured or single-stranded or treated to render it denatured or single-stranded. Such treatments are known in the art and include, for instance, heat or alkali treatment, or enzymatic digestion of one strand. For example, double stranded DNA (dsDNA) can be heated at 90-100° C. for a period of about 1 to 10 minutes to produce denatured material, while RNA produced via transcription from a dsDNA template is already single-stranded.

"Oligonucleotide" refers generally to a two or more covalently bonded nucleotides, usually single-stranded, usually a synthetic polynucleotide but may be a naturally occurring polynucleotide. The oligonucleotide(s) are usually comprised of a sequence of at least 5 nucleotides, for example, 10 to thousands of nucleotides, such as 2,000 to about 10,000, preferably, 20 to 250 nucleotides, more preferably, 20 to 125 nucleotides, and desirably about 60 nucleotides in length.

Various techniques can be employed for preparing an oligonucleotide. Such oligonucleotides can be obtained by biological synthesis or by chemical synthesis. For short sequences, such as up to about 100 nucleotides, chemical synthesis can frequently be more economical as compared to the biological synthesis. In addition to economy, chemical synthesis provides a convenient way of incorporating low molecular weight compounds, modified bases, or both, during specific synthesis steps. Furthermore, chemical synthesis can be very flexible in the choice of length and region of target polynucleotides binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single-stranded DNA as described in J. Messing (1983) *Methods Enzymol.*, 101:20-78.

Other methods of oligonucleotide synthesis include phosphotriester and phosphodiester methods (Narang, et al., (1979) *Meth. Enzymol.*, 68:90) and synthesis on a support (Beaucage, et al. (1981) *Tetrahedron Letters*, 22:1859-1862) as well as phosphoramidate techniques (Caruthers, M. H., et al., "Methods in Enzymology," Vol. 154, pp. 287-314 (1988)) and others described in "Synthesis and Applications of DNA and RNA," S. A. Narang, editor, Academic Press, New York, 1987, and the references contained therein. The chemical synthesis via a photolithographic method of spatially addressable arrays of oligonucleotides bound to glass surfaces is described by A. C. Pease, et al., *Proc. Nat. Acad. Sci., USA*, (1994) 91:5022-5026. Unless otherwise noted, terms oligonucleotide and polynucleotide are used interchangeably.

"Nucleotide" refers to the monomeric unit of nucleic acid polymers, i.e., DNA and RNA, whether obtained from a natural source or produced synthetically, which comprises a nitrogenous heterocyclic base, which is a derivative of a purine or pyrimidine, a pentose sugar, and a phosphate (or phosphoric acid). When the phosphate is removed, the monomeric unit that remains is a "nucleoside." Thus, a nucleotide is a 5'-phosphate of the corresponding nucleoside. When the nitrogenous base is removed from the nucleotide, the monomeric unit that remains is a "phosphodiester." "Nucleotide" can include its corresponding nucleoside and phosphodiester, and "oligonucleotide" can include its corresponding oligonucleoside and oligophosphodiester, unless indicated otherwise. The term "nucleotide" can include "modified nucleotide" that contains, for example, a modified base, sugar or phosphate group. The modified nucleotide can be produced by a chemical modification of a nucleotide either as part of the nucleic acid polymer or prior to the incorporation of the modified nucleotide into the nucleic acid polymer. For example, the methods mentioned above for the synthesis of an oligonucleotide may be employed. In another approach, a modified nucleotide can be produced by incorporating a modified nucleoside triphosphate into the polymer chain during an amplification reaction. Examples of modified nucleotides, by way of illustration and not limitation, include dideoxynucleotides, derivatives or analogs that are biotinylated, amine modified, alkylated, fluorophore-labeled, and like modifications, and can also include phosphorothioate, phosphite, ring atom modified derivatives, and like modifications.

"Target material" or "target" refers to a sequence of nucleotides to be identified, usually existing within a portion or all of a polynucleotide, usually a polynucleotide analyte. The identity of the target nucleotide sequence generally is known to an extent sufficient to allow preparation of various probe sequences hybridizable with the target material.

The target material usually contains from about 30 to 5,000 or more nucleotides, preferably 50 to 1,000 nucleotides. The target material is generally a fraction of a larger molecule or it may be substantially the entire molecule such as a polynucleotide as described above. The minimum number of nucleotides in the target material is selected to assure that the presence of a target polynucleotide in a sample is a specific indicator of the presence of polynucleotide in a sample. The maximum number of nucleotides in the target material is normally governed by several factors: the length of the polynucleotide from which it is derived, the tendency of such polynucleotide to be broken by shearing or other processes during isolation, the efficiency of any procedures required to prepare the sample for analysis, for example, transcription of a DNA template into RNA, and the efficiency of detection, amplification, or both, of the target nucleotide sequence, where appropriate.

"Nucleic acid probe" refers to an oligonucleotide or polynucleotide employed to bind to a portion of a polynucleotide such as another oligonucleotide or a target material. The design and preparation of the nucleic acid probes are generally dependent upon the sensitivity and specificity required, the sequence of the target material and, in certain cases, the biological significance of certain portions of the target material.

"Hybridization," "hybridizing," "binding" and like terms, in the context of nucleotide sequences, can be used interchangeably herein. The ability of two nucleotide sequences to hybridize with each other is based on the degree of complementarity of the two sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of co-solvents, lowering the salt concentration, and the like. Hybridization of complementary Watson/Crick base pairs of probes on the microarray and of the target material is generally preferred, but non-Watson/Crick base pairing during hybridization can also occur.

Conventional hybridization solutions and processes for hybridization are described in J. Sambrook, *Molecular Cloning: A Laboratory Manual*, (supra), incorporated herein by reference. Conditions for hybridization typically include (1) high ionic strength solution, (2) at a controlled temperature, and (3) in the presence of carrier DNA and surfactants and chelators of divalent cations, all of which are known in the art.

"Complementary" refers to two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence, to form Watson/Crick base pairs. RNA sequences can also include complementary G=U or U=G base pairs. Non-standard or non-Watson/Crick base pairing is also possible with nucleotide complements, for instance, the sequences may be parallel to each other and complementary A=C or G=U base pairs in RNA sequences or complementary G=T or A=C base pairs in DNA sequences can occur, although not preferred.

"Substrate" or "substrate surface" refers to a porous or non-porous water insoluble support material. The substrate can have any one of a number of shapes, such as strip, plate, disk, rod, particle, including bead, and the like. The substrate surface can be hydrophobic or hydrophilic or capable of being rendered hydrophobic or hydrophilic and can include, for example, inorganic powders such as silica, magnesium sulfate, and alumina; natural polymeric materials, particularly cellulosic materials and materials derived from cellulose, such as fiber-containing papers, e.g., filter paper, chromatographic paper, and like materials; synthetic or modified naturally occurring polymers, such as nitrocellulose, cellulose acetate, poly(vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), and like materials; either used alone or in conjunction with other materials; glass available as Bioglass, ceramics, metals, and like materials. Natural or synthetic assemblies such as liposomes, phospholipid vesicles, and cells can also be employed.

Common substrates used for arrays in accordance with the present disclosure are surface-derivatized glass or silica, or polymer membrane surfaces, as described in Z. Guo, et al., *Nucleic Acids Res,* 22, 5456-65 (1994); U. Maskos, E. M. Southern, *Nucleic Acids Res,* 20, 1679-84 (1992), and E. M. Southern, et al., *Nucleic Acids Res,* 22, 1368-73 (1994), each incorporated by reference herein. In modifying siliceous or metal oxide surfaces, one technique that has been used is derivatization with bifunctional silanes, i. e., silanes having a first functional group enabling covalent binding to the surface (often an Si-halogen or Si-alkoxy group, as in —$SiCl_3$ or —$Si(OCH_3)_3$, respectively) and a second functional group that can impart the desired chemical and/or physical modifications to the surface to covalently or non-covalently attach ligands and/or the polymers or monomers for the biological probe array. Silylated derivatizations and other surface derivatizations that are known in the art are within the scope of the disclosure. See for example U.S. Pat. No. 5,624,711 to Sundberg, U.S. Pat. No. 5,266,222 to Willis, and U.S. Pat. No. 5,137,765 to Farnsworth, each incorporated by reference herein. Other processes for preparing arrays are described in U.S. Pat. No. 6,649,348, to Bass et. al., assigned to Agilent Corp., which disclose DNA arrays created by in situ synthesis methods.

Immobilization of oligonucleotides on a substrate or surface can be accomplished by well-known techniques, commonly available in the literature. See for example A. C. Pease, et al., *Proc. Nat. Acad. Sci*, USA, 91:5022-5026 (1994); Z. Guo, et al., *Nucleic Acids Res,* 22, 5456-65 (1994); and M. Schena, et al., *Science,* 270, 467-70 (1995), each incorporated by reference herein.

"Siliceous substrate" refers to any material largely comprised of silicon dioxide. Silylated siliceous substrate is a siliceous substrate that has at least one surface derivatized with a silane compound using materials and methods known in the art to facilitate the bonding of nucleic acid probes.

"Bubble" refers to a small ball of gas in a fluid. The word "bubble" used alone encompasses both a gas bubble and a vapor bubble.

"Set" or "sub-set" of any item, such as a set of proteins or peptides, may contain only one of the item, or only two, or three, or any multiple number of the items.

A "peptide mixture" is typically a complex mixture of peptides obtained as a result of the cleavage of a sample comprising proteins.

A "sample of proteins" is typically any complex mixture of proteins and/or their modified and/or processed forms, which may be obtained from sources, including, without limitation: a cell sample (e.g., lysate, suspension, collection of adherent cells on a culture plate, a scraping, a fragment or slice of tissue, a tumor, biopsy sample, an archival cell or tissue sample, laser-capture dissected cells, and like sources), an organism (e.g., a microorganism such as a bacteria or yeast), a subcellular fraction (e.g., comprising organelles such as nuclei or mitochondria, large protein complexes such as ribosomes or golgi, and like sources), an egg, sperm, embryo, a biological fluid, viruses, and like sources.

"Peptide" refers to an entity comprising at least one peptide bond, and can comprise either D and/or L amino acids. A peptide can have, for example, about 2 to about 20 amino acids (e.g., about 2, 3, 4, 5, 6, 7, 8, 9, or 10 amino acids).

"Protein" refers to any protein, including, but not limited to peptides, enzymes, glycoproteins, hormones, receptors, antigens, antibodies, growth factors, and like natural or synthetic molecules, without limitation. Proteins include those comprised of greater than about 20 amino acids, greater than about 35 amino acid residues, or greater than about 50 amino acid residues.

"Peptide," "polypeptide," and "protein" are generally used interchangeably herein.

A "biological fluid" includes, but is not limited to, for example, blood, plasma, serum, sputum, urine, tears, saliva, sputum, cerebrospinal fluid, ravages, leukapheresis samples, milk, ductal fluid, perspiration, lymph, semen, umbilical cord fluid, and amniotic fluid, as well as fluid obtained by culturing cells, such as fermentation broth and cell culture medium.

A "sample of complex proteins" may contain, for example, greater than about 100, about 500, about 1,000, about 5,000, about 10,000, about 20,000, about 30,000, about 100,000 or more different proteins. Such samples may be derived from a natural biological source (e.g., cells, tissue, bodily fluid, soil or water sample, and the like) or may be artificially generated (e.g., by combining one or more samples of natural and/or synthetic or recombinant sources of proteins).

"Expression" refers to a level, form, or localization of product. For example, "expression of a protein" refers to one or more of the level, form (e.g., presence, absence or quantity of modifications, or cleavage or other processed products), or localization of the protein.

"Proteome" refer to the protein constituents expressed by a genome, typically represented at a given point in time. A "sub-proteome" is a portion or subset of the proteome, for example, the proteins involved in a selected metabolic pathway, or a set of proteins having a common enzymatic activity.

A "remote location," refers to location other than the location at which the hybridization and/or array analysis occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart.

"Communicating information" refers to transmitting the data representing that information as signals (e.g., electrical, optical, radio, magnetic, etc) over a suitable communication channel (e.g., a private or public network).

A component of a system which is "in communication with" or "communicates with" another component of a system receives input from that component and/or provides an output to that component to implement a system function. A component which is "in communication with" or which "communicates with" another component may be, but is not necessarily, physically connected to the other component. For example, the component may communicate information to the other component and/or receive information from the other component. "Input" or "output" may be in the form of electrical signals, light, data (e.g., spectral data), materials, or may be in the form of an action taken by the system or component of the system. The term "in communication with" also encompasses a physical connection that may be direct or indirect between one system and another or one component of a system and another.

"Forwarding" an item refers to any means of getting that item from one location to the next, whether by physically transporting that item or otherwise (where that is possible) and includes, at least in the case of data, physically transporting the data or communicating the data.

A "computer-based system" refers to the hardware means, software means, and data storage means used to analyze the information of the present disclosure. The minimum hardware of the computer-based systems of the present disclosure comprises a central processing unit (CPU), input means, output means, and data storage means. A skilled artisan can readily appreciate that any one of the currently available computer-based system are suitable for use in the present disclosure. The data storage means may comprise any manufacture comprising a recording of the present information as described above, or a memory access means that can access such a manufacture. In certain instances a computer-based system may include one or more wireless devices.

To "record" data, programming or other information on a computer readable medium refers to a process for storing information, using any such methods as known in the art. Any convenient data storage structure may be chosen, based on the means used to access the stored information. A variety of data processor programs and formats can be used for storage, for example, word processing text file, database format, and like formats.

A "processor" refers to any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

A "database" is a collection of information or facts organized according to a data model, which determines whether the data is ordered using linked files, hierarchically, according to relational tables, or according to some other model determined by the system operator.

An "information management system" refers to a program, or series of programs, which can search a database and determine relationships between data identified as a result of such a search.

An "interface on the display of a user device" or "user interface" or "graphical user interface" is a display (comprising text and/or graphical information) displayed by the screen or monitor of a user device connectable to the network which enables a user to interact with a system processor and/or system memory (e.g., including a data base and information management system).

"Providing access to at least a portion of a database" refers to making information in the database available to user(s) through a visual or auditory means of communication.

"Separation" refers to dividing, partially or completely, a substance, such as a nucleotide or protein mixture, into its component parts, such as like similar protein molecules or complementary hybridization of a nucleotide or nucleotide mixture, and optionally the removal of impurities. "Separation" can also refer to resolution of a signal peak, for example, from a near-by signal, from noise, or combinations thereof.

"Assessing" and "evaluating" are used interchangeably to refer to any form of measurement, and includes determining if an element is present or not.

"Determining," "measuring," "assessing," "assaying" and like terms are used interchangeably and can include both quantitative and qualitative determinations. Assessing may be relative or absolute. "Assessing the presence of" includes determining the amount of something present, as well as determining whether it is present or absent.

It must be noted that as used herein and in the appended claims, the singular forms "a", "and", and "the" include plural referents unless the context clearly dictates otherwise. Thus, for example, reference to "a protein" can include a plurality of such proteins and reference to "protein" can include reference to one or more proteins and equivalents thereof known to those skilled in the art.

"About" modifying, for example, the quantity of an ingredient in a composition, concentrations, volumes, process temperatures, process times, recoveries or yields, flow rates, and like values, and ranges thereof, employed in describing the embodiments of the disclosure, refers to variation in the numerical quantity that can occur, for example, through typical measuring and handling procedures; through inadvertent error in these procedures; through differences in the ingredients used to carry out the methods; and like proximate considerations. The term "about" also encompasses amounts that differ due to aging of a formulation with a particular initial concentration or mixture, and amounts that differ due to mixing or processing a formulation with a particular initial concentration or mixture. Whether modified by the term "about" the claims appended hereto include equivalents to these quantities.

Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

We have discovered that high efficiency substrate wetting agents, or superwetting agents, in the hybridization buffer composition provide many improvements and benefits as illustrated herein. Although detergents such as lithium dodecyl sulfate and Triton X-102 have been reported as components of hybridization solutions (e.g., EP1186671 A2, now abandoned), the use of surface active materials that possess highly efficient surface wetting properties, in contrast to detersive agents, provide superior and unexpected results. Superwetting agents are known and typically sold for use as formulation additives in, for example, paints, lacquers, coatings, inks, and like formulations.

The present disclosure provides, in embodiments, an improved hybridization buffer composition which can:

improve the ability of a hybridization composition to wet the surface of the microarray;

keep the surface of the microarray wetted under a wider range of conditions;

improve the ability of bubbles to move reliably in an hybridization chamber;

enable the use of hybridization chambers having smaller volumes, narrower thicknesses, or both;

enable a wider range of rotational speeds during the hybridization mixing process; and enable or improve the performance of non-bubble mixing methods.

Additionally, the superwetting agents of the present disclosure can be low-foaming and can advantageously provide anti-foam properties to the method and composition.

Particularly preferred superwetting agents of the disclosure are those compounds or compositions that are water soluble or dispersible that can be used with water-based systems to impart very high wetting and very low surface tension to the contacted surface. Concentrations of superwetting agent in the contacting formulations can range, for example, from about 0.01% to 50% by weight or volume, from about 0.05% to 20% by weight or volume, and from about 0.1% to 10% by weight or volume, based on the total weight (w/w) or volume (w/v) of the buffer composition.

Superwetting agents useful in the present method and composition include, for example, silicone based surfactants such as silicone polyoxyalkylene copolymers. Such materials are commercially available, for example, as TEGO® Wet 260, TEGO® Wet 280, TEGO® Wet KL 245. Superwetting polyether siloxane copolymers, or alternatively referred to as silicone polyoxyalkylene copolymers, such as TEGO® Wet 260, are commercially available from Tego Chemie Service, GmbH, formerly Goldschmidt Chemicals. Other examples of silicone surfactant as superwetting can be found in *Silicone Surfactants*, R. M. Hill, ed., Marcel Dekker, 1999. Other suitable superwetting agents include, for example, fluorocarbon surfactants, such as Zonyl® and Novec®, and the hydrocarbon-based surfactants, such as TEGO® Wet 510, Dynol®, Surfynol®, and EnviroGem® surfactants.

Superwetting agents such as TEGO® Wet 260 are miscible with water in all concentrations at room temperature. However, at the elevated temperatures that are sometimes required for DNA array hybridization, for example 65° C., phase separation of the TEGO® Wet 260 surfactant from the aqueous buffer may be observed depending upon, for example, the amount of the superwetting agent, the presence or absence of other components in the buffer composition, and like considerations. The presence of an additional surfactant such as lithium dodecyl sulfate (LiDS) has been found to prevent this phase separation. The amount of LiDS required to prevent this phase separation is a function of the amount of TEGO® Wet 260 added to the buffer composition. In embodiments, suitable formulations are preferably formulated to contain sufficient LiDS, or an equivalent material, to prevent phase separation at, for example, about 65° C.

In embodiments, the superwetting agent can comprise an organosilicone wetting agent, an organofluorine wetting agent, a hydrocarbyl wetting agent, and like superwetting materials, or mixtures thereof. Superwetting agents employed in the present method and composition include, for example, certain organosilicone-based surfactants, for example, having the general formula:

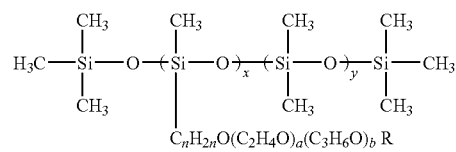

wherein x is from about 1 to about 10; y is from about 0 to about 10; n is from about 3 to about 4; a is from about 0 to about 15; b is from about 0 to about 14; such that at least one of a and b is not zero and a+b is from about 1 to about 30; and R can be, for example, hydrogen, an alkyl group having from about 1 to about 4 carbon atoms, an acetyl group, and mixtures thereof. Other like structural variants are believed to be suitable, such as where the alkoxylation can be, additionally or alternatively, in the organosilicone copolymer backbone.

Examples of specific superwetting agents are disclosed in U.S. Pat. No. 6,503,413, to Uchiyama, et al., issued Jan. 7, 2003, such as a polyalkyleneoxide polysiloxane having the formula:

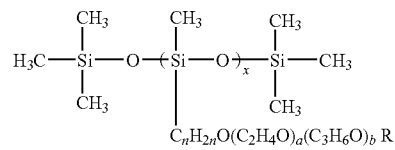

wherein x is from about 1 to about 8; n is from about 3 to about 4; a is from about 1 to about 15; b is from about 0 to about 14; a+b is from about 5 to about 15; and R is selected from the group consisting of hydrogen, an alkyl group having from about 1 to about 4 carbon atoms, and an acetyl group. The polyalkylene polysiloxane can have a molecular weight of from about several hundred to many thousands, for example, less than about 1,000 to 10,000.

Still other superwetting agents suitable for use in the present method and composition include certain organosilicone-based and fluorocarbon-based surfactants, as disclosed for example in U.S. Pat. No. 5,985,793, to Sandbrink, et al., issued Nov. 16, 1999, such as a polyalkyleneoxide polysiloxane having the formula:

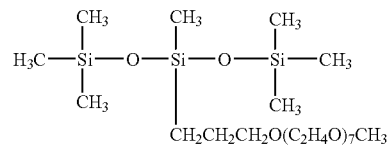

and like polyether siloxane copolymers.

U.S. Pat. No. 4,380,451, to Steinberger, issued Apr. 19, 1983, discloses continuous dyeing and simultaneous finishing of textile materials using defoaming agent of polyoxyalkylene polysiloxane copolymer and hydrophobic silica, including a method for preparing the polyoxyalkylene polysiloxane copolymer material, see Example I. U.S. Pat. No. 4,728,457, to Fieler, et al., issued Mar. 1, 1988, discloses non-volatile silicone fluids that can be, for example, a polyalkyl siloxane, a polyaryl siloxane, a polyalkylaryl siloxane, or a polyether siloxane copolymer. Other disclosures of suitable silicone fluids include U.S. Pat. No. 2,826,551, to Geen, U.S. Pat. No. 3,964,500, to Drakoff, U.S. Pat. No. 4,364,837, to Pader, and British Pat. No. 849,433, to Woolston. All of these patents are incorporated herein by reference. Also incorporated herein by reference is *Silicon Compounds* distributed by Petrarch Systems, Inc., 1984. Another source of siloxanes, silicones, and related compounds, useful in the present disclosure is, for example, Gelest, Inc., reference the 1995 catalog and www.gelest.com. Still other silicone material that can be useful in the present compositions include silicone gums described by Petrarch and others, including U.S. Pat. No. 4,152,416, Spitzer et al., and Noll, Walter, *Chemistry and Technology of Silicones*, New York: Academic Press 1968. U.S. Pat. No. 5,156,834, to Beckmeyer, et al., discloses antiperspirant compositions including a non-volatile emollient such as a polyalkyl siloxane, a polyalkylaryl siloxane or a polyether siloxane copolymer. These siloxanes are available, for example, from the General Electric Company as the Vicasil series and from Dow Corning as the Dow Corning 200 series. EP-A 633 018 discloses the use of polyoxyalkylenepolydimethylsiloxanes and like copolymers can be prepared, for example, by hydrosilylation in the presence of a platinum-containing catalyst. See also J. B. Plumb and J. H. Atherton, *Block Copolymers*, publisher; D. C. Allport and W. H. Janes, Applied Science Publishers Ltd., London, 1973, page 305-325. Copolymers are known in which polyoxyalkylene groups, as well as long-chain hydrocarbon groups are linked to a linear polysiloxane. The synthesis of such compounds is described in U.S. Pat. Nos. 3,234,252, 4,047,958, 4,427,958, 3,427,271 and 2,846,458. The synthesis can be accomplished by adding an olefin with, for example, 6 to 18 carbon atoms, and a polyoxyalkylene ether of an olefinically unsaturated alcohol, e.g., the polyoxyalkylene ether of allyl alcohol, to a polydiorganosiloxane having SiH groups, the addition being carried out in the presence of a catalyst containing platinum. Ethoxylated organosilicone wetting agents are also disclosed in U.S. Pat. Nos. 5,985,793, 4,160,776, 4,226,794, and 4,337,168, the disclosures of which are incorporated herein by reference.

Still other examples of suitable polyalkyleneoxide polysiloxane surfactants are commercially available under the trade names Silwet® L-77, Silwet® L-7280, and Silwet® L-7608 available from Witco Corporation; and DC Q2-5211 and Sylgard® 309 available from Dow Corning Corporation.

Fluorocarbon-based superwetting agent can be, for example, an organofluorine compound of the formulas:

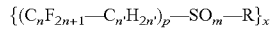  a)

wherein m is for 1 to 3; n is from about 3 to about 20; n' is from about 0 to about 20; p is from 1 to 2; x is from about 1 to about 100; R is hydrogen, $(C_{1-10})$ saturated alkyl, or $(C_{2-10})$ unsaturated alkyl; or salts thereof;

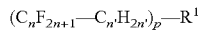  b)

wherein
$R^1$ is monovalent or divalent radical selected from the group
—H,
halo, such as —Cl, —Br, —I,
—OH,
$(C_{1-10})$ alkyl,
$(C_{2-10})$ unsaturated alkyl,
—CH$_2$—O—C(=O)—$(C_{1-20})$ alkyl,
—CH$_2$—O—C(=O)—$(C_{2-20})$ unsaturated alkyl,
—O—P(=O)(OH)$_2$,
—O—P(=O)(—OH)—,
—O—P(=O)(OH)(—O—CH$_2$—CH$_2$—)$_o$—OH,
—CO$_2$H,
—$^{(+)}$N(R$^2$)$_2$—O$^{(-)}$,
—$^{(+)}$N(R$^2$)$_2$—CH$_2$—CO$_2$H,
—O—C(=O)—CH$_2$—CH(SO$_3$H)—C(=O)—O—,
—O(CH$_2$—CH$_2$—O)$_y$—H,
—S—CH$_2$—CH$_2$—C(=O)—OH, or
$(C_{1-10})$alkyl-C(=O)—O—CH—CH$_2$—$^{(+)}$N(R$^2$)$_2$—(CH$_2$)$_{1-4}$—CO$_2$H,
each $R^2$ is independently hydrogen, or $(C_{1-10})$ alkyl,
m is for 1 to 2;
n is from about 1 to about 20;
n' is from about 1 to about 20;
o is from about 1 to about 10;
p is for 1 to 2; and
y is from 0 to about 20;
or salts thereof;

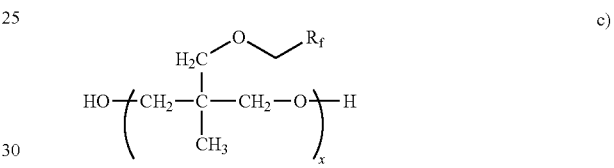  c)

wherein
$R_f$ is a monovalent radical of the formula —$C_nF_{2n+1}$;
n is from about 1 to about 20; and
x is for 1 to 100;
or salts thereof,
and like or equivalent compounds including polymers thereof where compounds a), b), or c) can be polymerized, and mixtures thereof.

Compounds of the above formula a) are known, for example, as Novec™ fluorosurfactants and are available from 3M Company. Compounds of the formula b) are known, for example, as Marsurf FS—fluorosurfactants and are available from Mason Chemical Company, and as Zonyl® and Forafac® fluorinated surfactants or intermediates, and are available from DuPont Company. Compounds of the formula c) are known as PolyFox products and are available from OMNOVA Solutions, Inc. (www.omnova.com).

Preferred compounds of the formula $C_nF_{2n+1}$—SO$_m$R can be, for example, non-ionic and anionic sulfonyl compounds and polymers thereof, and which products are commercially available as Novec™ fluorosurfactants (replacing 3M Fluorad™ fluorosurfactants) from 3M Company, such as the perflurobutanesulfonates. In the formula $C_nF_{2n+1}$—SO$_m$R the carbon chain in $C_nF_{2n+1}$ and the $(C_{1-10})$ alkyl or $(C_{2-10})$ unsaturated alkyl selections for R, as with other alkyl substituents of the disclosure, can be linear, branched, cyclic, or mixtures thereof. Specific Novec™ superwetting materials include non-ionic polymeric fluorosurfactant products FC-4432 and FC-4430.

Still other superwetting agent of the disclosure can be, for example, hydrocarbon-based or hydrocarbyl wetting agent, such as an alkoxylated hydrocarbyl compound of the formula:

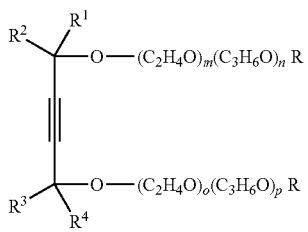

wherein

R is hydrogen or an alkyl radical having from 1 to 4 carbon atoms, $R^1$ to $R^4$ are each independently hydrogen or an alkyl radical having from 3 to 10 carbon atoms; and m, n, o and p are from 0 to 30 and a sum of 3 to about 60, inclusive. The alkoxylated copolymer units comprised of m and o units which represent ethylene oxide adducts (EO) and n and p units which represent propylene oxide adducts (PO), when either or both m+n or o+p are present, can be, for example, random EO—PO mixtures, block EO—PO, gradient EO—PO mixtures, alternating EO—PO mixtures, segmented EO—PO mixtures, and like combinations, or mixtures thereof. The alkoxylated copolymer units represented by m and n, and o and p, can be in any order, such as —O-(EO)$_m$—(PO)$_n$—R or —O(PO)$_n$-(EO)$_m$—R. U.S. Pat. No. 6,313,182, assigned to Air Products, discloses an acetylenic diol ethylene oxide/propylene oxide adduct for example, an acetylenic glycol compound or alternatively referred to as an ethoxylated acetylenic diol compound available as Dynol™ surfactants from Air Products Corporation, such as Dynol™ 604 and ethoxylated and ethoxylated/propoxylated products such as Surfynol™, and EnviroGem™ AE Surfactants. The following U.S. patents also describe various acetylenic alcohols and their ethoxylates as surface active agents: U.S. Pat. No. 3,268,593 (ethylene oxide adducts of tertiary acetylenic alcohols); U.S. Pat. No. 4,117,249 (3 to 30 mole ethylene oxide (EO) adducts of acetylenic glycols); and U.S. Pat. No. 5,650,543. Specific acetylenic diol-ethylene oxide adducts include the ethylene oxide adducts of, for example, 3-methyl-1-nonyn-3-ol, 7,10-dimethyl-8-hexadecyne-7,10-diol; 2,4,7,9-tetramethyl-5-decyne-4,7-diol and 4,7-dimethyl-5-decyne-4,7-diol.

Yet still other superwetting agent of the disclosure can be any other similar or any other proprietary material which can provide the desired wetting characteristics and hybridization results, for example, EnviroGem™ defoaming wetting agents, such as AD01, commercially available from Air Products Corp., which have a dual hydrophobe and dual hydrophile structure (i.e., a dimeric or gemini surfactant).

The present disclosure also provides, in embodiments, a method of modifying a surface, for example, a method of hybridizing a microarray of a first oligonucleotide bound to a surface, for example, a modified siliceous substrate, with a second unbound oligonucleotide material, comprising: contacting the microarray with an aqueous mixture comprising a superwetting agent. In embodiments, the method of hybridizing can be accomplished with an aqueous mixture comprising a superwetting agent used as a conditioning formulation prior to or after hybridization or contacting with a second unbound oligonucleotide material.

In embodiments, the method of hybridizing can be accomplished with an aqueous mixture, which can include for example a second oligonucleotide material. In embodiments, the method of hybridizing can also further comprise a second contacting of the microarray with an aqueous mixture comprising a superwetting agent and a second oligonucleotide material. The second contacting can include one or more, such as a plurality of contacting steps of the microarray with the same or different aqueous mixture and oligonucleotide material, for example, to accomplish aggregate screening of samples for selected genomic content, or to detect or measure changes in genomic properties of a sample source over time.

The buffer capacity and the pH of the aqueous mixture containing the superwetting agent can be at, for example, from about 5 to about 9, from about 5 to about 8, from about 5 to about 7, from about 5 to about 6, and like pH values, such as from about 5.5 to about 6.7, in embodiments. The contacting can be accomplished at various temperatures known to those skilled in the art, for example, from about 30° C. to about 70° C., from about 40° C. to about 70° C., from about 50° C. to about 70° C., from about 50° C. to about 65° C., from about 55° C. to about 65° C., and like temperatures.

In a preferred embodiment the contacting can be accomplished with an apparatus which provides a dispelling bubble, for example, a moving or a collapsing gas bubble, such as a rotating gas bubble, see for example, U.S. Pat. Nos. 6,513,968, and 6,186,659, to Schembri. These patents disclose methods and apparatus for mixing a film of fluid, and for example performing array hybridization with bubbles. U.S. Pat. Nos. 6,613,529, and 6,420,114, to Bedilion et. al., also disclose bubble mixing methods.

In embodiments, the method and composition of the present disclosure can include in the aqueous mixture, in addition to a superwetting agent, additional performance enhancing components, for example, one or more of: an organosulfonic acid; an organosulfate surfactant; an organopolyalkoxylate; a source of a monovalent cation; a chelator; or mixtures thereof. In embodiments, the composition of the present disclosure includes a buffer concentrate comprising: a superwetting agent and a buffer component. The buffer concentrate can comprise any suitable buffer such as an organic compound, an inorganic compound, or mixtures thereof, and as illustrated herein.

The buffer concentrate can, for example, further comprise one or more of:

a source of a monovalent cation;

a water soluble organosulfonic acid or salt thereof;

a chelator or salt thereof;

an organosulfate surfactant or salt thereof;

an organopolyalkoxylate;

an aqueous carrier;

or mixtures thereof.

The source of a monovalent cation can be, for example, an alkali metal halide salt, such as lithium, sodium, potassium halide salts, e.g., LiCl, and like salts, or mixtures thereof. The organosulfonic acid can be, for example, a morpholino-substituted alkyl sulfonic acid, such as MES, MOPS, and like materials. The chelator can be, for example, a divalent cation chelating agent, such as EDTA and like chelators, or mixtures thereof. The organosulfate surfactant can be, for example, a ($C_8$-$C_{16}$) alkyl sulfate, such as a sodium or lithium dodecylsulfate (LiDS)(laurylsulfate, n-$C_{12}H_{25}$—$OSO_3^-$), and like surfactants, or mixtures thereof. The organopolyalkoxylate can be, for example, an alkoxylated alkylphenol, such as Triton X-100, 4-octylphenol polyethoxylate, molecular formula: $C_{14}H_{22}O(C_2H_4O)_nH$ where the average number of ethylene oxide units per molecule is around 9 or 10 (CAS No: 9002-93-1), and like materials, or mixtures thereof.

The superwetting agent can be, for example, present in from about 0.05 to about 50 weight percent of the total concentrate. The water soluble organosulfonic acid can be present in from about 0.01 to about 10 weight percent of the total concentrate. The organosulfate surfactant can be, for example, present in from about 0.1 to about 50 weight percent of the total concentrate. The organopolyalkoxylate can be, for example, present in from about 0.1 to about 50 weight percent of the total concentrate. The chelator can be, for example, present in from about 0.01 to about 10 weight percent of the total concentrate. The source of a monovalent cation can be, for example, present in from about 0.01 to about 50 weight percent of the total concentrate. The aqueous carrier, such as water, can be, for example, absent or minimized in the concentrate, or provided to balance the buffer concentrate or composition to achieve convenient storage or use concentrations, for example, 1× use concentrations, and 2×, 3×, 4×, 5×, and like n× concentrates where n is a multiplier integer or a fraction thereof. In embodiments, the aqueous carrier can include other ingredients, for example, dissolved urea, formamide, and like compounds or cosolvents. In embodiments, the carrier can alternatively comprise non-aqueous media, for example, formamide, DMSO, and like liquids. The compositions of the present disclosure, in embodiments, can comprise an aqueous carrier that comprises water. The water used can be distilled, deionized, or tap water. The amount of water in the present compositions can vary dependent upon the specific uses of the composition. The component parts of the formulation add up to 100 weight percent or alternatively parts by weight. A buffer concentrate can have, for example, a pH from about 4 to 10, and use compositions can have any suitable intermediate pH and as illustrated herein.

The present disclosure provides a method and a composition for hybridizing nucleic acid microarrays with other nucleic acid materials used, for example, in high throughput analytical, therapeutic, and diagnostic applications. The method uses hybridization conditions, which are advantageously compatible with siliceous substrates and surface-derivatized siliceous substrates, for performing assays, for example, at high hybridization temperatures for long periods of time. In embodiments, the substrates are hydrophobic, such as polymer coated surfaces, see for example, U.S. Pat. Nos. 6,444,268, and 6,258,454, to Lefkowitz et. al., assigned to Agilent Corp., which patents disclose silane chemistry and surface modification for creating substrates for DNA arrays having moderately hydrophobic surfaces. The present disclosure provides hybridization compositions and conditions that work particularly well on, for example, silane-derivatized siliceous substrates ("silylated-siliceous" substrates). The hybridization conditions of the present disclosure can include solution pH, buffer type, salt composition, surfactant composition, temperature, and time. The present disclosure allows sensitive, selective detection of nucleic acid targets, while preserving the integrity and stability of the derivatized siliceous surface. In embodiments, the method of the present disclosure solves a problem of substrate receptivity by enhancing substrate surface wetting when preparing or performing assays on derivatized siliceous substrates, for example, at elevated hybridization temperatures such as from about 55° C. to about 70° C. for time periods used to hybridize a target material. The method of the disclosure also provides superior hybridization assay performance by maintaining the integrity of the derivatized surface of the siliceous substrates.

In one aspect of the disclosure, a method of hybridizing nucleic acid microarrays on surface derivatized-siliceous substrates with another nucleic acid material is provided. The method comprises the steps of maintaining a hybridization solution at a pH between pH 5 and 7, and incubating the nucleic acid microarray with the nucleic acid material in the pH-maintained hybridization buffer composition at a hybridization temperature ranging from about 55° C. to about 70° C. In one embodiment of the method of hybridizing, the hybridization solution is maintained at a pH between pH 5.5 and 6.7 with a buffer having buffering capacity between pH 5.5 and 6.7, and having a monovalent cation present. Preferably, the pH is maintained between pH 6.0 and 6.6; the buffer is selected from one or more of MES or MOPS; and the monovalent cation is provided by a salt preferably selected from one or more of LiCl, NaCl, or KCl. The hybridization temperature can preferably ranges from about 60° C. to 66° C. In another embodiment, the hybridization buffer composition can further comprise one or more of a chelating agent and a surfactant.

A hybridization assay, in embodiments, can take anywhere from less than about 2 hours to more than 48 hours, depending on at least the type and complexity of the hybridization experiment. The problem in the art with dissolution of surface derivatized-siliceous substrates is more evident for hybridizations taking about 8 hours and more to complete at high hybridization temperatures. By "complete", it is meant that a desired amount of hybridization of the target nucleic acid material is achieved, which is both user and target material dependent. The present method and composition perform well where conventional hybridization parameters fail, for example, at a hybridization time of about 6 hours and longer. The present method and composition perform particularly well for hybridizations taking at least 24 hours to complete, and more particularly, for hybridizations taking between about 12 hours to at least 24 hours.

In another aspect of the present disclosure, a method of hybridizing a microarray of an oligonucleotide bound to a silylated-siliceous substrate with another oligonucleotide material is provided. The method of hybridizing comprises the steps of combining the oligonucleotide material with a hybridization buffer composition having a pH between pH 5.5 and 6.7 comprising a buffer and a monovalent cation; and incubating the material in the buffered composition with the oligonucleotide microarray at a hybridization temperature ranging from about 55° C. to about 70° C. to hybridize the oligonucleotide material. The incubation time period can range, for example, from less than about 2 hours to more than 48 hours. The method is particularly useful where conventional hybridization parameters fail on silylated-siliceous substrates at high temperature. Preferably, the buffer can be selected from one or more of and organosulfonic acid such as MES or MOPS, which has a buffering capacity within the pH range of pH 5.5 and 6.7. The monovalent cation can be provided by a salt, such as an alkali halide, preferably selected from one or more of LiCl, NaCl, KCl, and mixtures thereof. Moreover, the hybridization temperature preferably ranges from about 60° C. to 66° C. More preferably, the hybridization buffer composition can further comprise one or more of a chelating agent and a surfactant.

The method and composition of the present disclosure may overcome problems in the art by, for example, minimizing degradation of the surface derivatization of the siliceous substrate and further, etching of the substrate, both of which can impact the hybridization results between nucleic acid probes and target materials at elevated temperatures. Further, the method and the composition of the present disclosure do not affect the signal intensities of the signal labeling system used in conventional hybridization assays. The hybridization conditions and methods of the present disclosure are particularly useful in DNA or RNA microarray assays performed at elevated temperatures, for example, above about 55° C., and for longer hybridization times, such as, greater than about 6 hours, where conventional buffer compositions, including but not limited to SSC, SSPE, Tris-Cl, having high pH (e.g., pH≧6.8) buffering capacity that can react with the conventional siliceous substrates that have been derivatized, and can affect hybridization results.

In still another aspect of the disclosure, a kit is provided that comprises a microarray of an oligonucleotide on a derivatized surface of a siliceous substrate and instructions for performing a hybridization assay using the microarray. The instructions comprise the method, the composition, or both, of the present disclosure. In one embodiment, the kit further comprises a hybridization composition having a superwetting agent, and preferably a pH maintained, for example, between pH 5.5 and 6.7, and preferably using a buffer having a useful buffering capacity in that pH range.

The composition and preparative methods of the present disclosure can be used to prepare custom or made-to-order array articles, such as a specific unhybridized array or a specific hybridized array.

The buffer compositions of the present disclosure can also be used in an article of manufacture comprising the composition contained in a suitable container, dispenser, or combination thereof. Preferably the articles of manufacture are in association with instructions for how to use the composition in array hybridization and like applications, including, for example, the manner, the amount, or both of the composition to use, and preferred ways to use. It is desirable that the instructions be as simple and clear as possible, so that using pictures or symbols may be desirable. Thus, a set of instructions can comprise an instruction to prepare a buffer concentrate or a working buffer, by following one or more of the described methods. A set of instructions can also comprise an instruction to use a buffer concentrate or a working buffer to prepare an array or hybridize an array. "In association with" refers to the set of instructions that can be either directly printed on the container or a container label, or presented in a separate manner including, but not limited to, a brochure, print advertisement, electronic advertisement, verbal communication, and like presentations, to communicate the set of instructions to a consumer or user of the article of manufacture. The set of instructions preferably comprises the instruction to apply an effective amount of the composition, preferably by contacting the working buffer with the array, to provide the indicated benefit, for example, array formation or array hybridization.

The compositions can be packaged in a bottle, especially a bottle that comprises a measuring closure. The measuring closure provides a convenient way to dispense the appropriate amount of the composition, especially when dispensing concentrated compositions into a more dilute solution or mixture. The bottle also preferably comprises a drain-back spout, which permits the composition to be dispensed more easily and with less waste or spillage. Non-limiting examples of suitable bottles are described in detail in U.S. Pat. No. 4,666,065, to Ohren; U.S. Pat. No. 4,696,416, to Muckenfuhs et al.; and U.S. Pat. No. 4,981,239, to Cappel et al.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the claims appended hereto.

Materials and Methods

Buffering Agents

The buffer compositions comprising a superwetting agent of the disclosure preferably include a buffering agent and obtain additional benefits therefrom. For example, low molecular weight polyalkyleneoxide polysiloxane surfactants may be unstable, especially if the pH of the compositions is not carefully controlled. The pH of the present compositions can be controlled within the ranges of from about 4 to about 10, preferably from about 5 to about 9.5, and more preferably from about 6 to about 9. The buffering agent can be any organic or inorganic, acid or base, and alkali metal salts thereof, having at least one $pK_a$ value and/or $pK_b$ value of from about 4 to about 10, preferably from about 5 to about 9.5, and more preferably from about 6 to about 9. Preferably, the buffering agent is an alkali metal salt of an organic acid and/or inorganic acid having at least one $pK_a$ value of from about 6 to about 9. It is recognized that buffering agents may have more than one $pK_a$ value and/or $pK_b$ value. A buffering agent preferably has at least one of its $pK_a$ values and/or $pK_b$ values within the indicated ranges.

Suitable buffering agents can be, for example, acridine, phenylalanine, allothreonine, n-amylamine, aniline, n-allylaniline, 4-bromoaniline, 4-bromo-N,N-dimethylaniline, m-chloroaniline, p-chloroaniline, 3-chloro-N,N-dimethylaniline, 3,5-dibromoaniline, N,N-diethylaniline, N,N-dimethylaniline, N-ethylaniline, 4-fluoroaniline, N-methylaniline, 4-methylthioaniline, 3-sulfonic acid aniline, 4-sulfonic acid aniline, p-anisidine, arginine, asparagine, glycyl asparagine, DL-aspartic acid, aziridine, 2-aminoethylbenzene, benzidine, benzimidazole, 2-ethylbenzimidazole, 2-methylbenzimidazole, 2-phenylbenzimidazole, 2-aminobenzoic acid, 4-aminobenzoic acid, benzylamine, 2-aminobiphenyl, brucine, 1,4-diaminobutane, t-butylamine 4-aminobutyric acid, glycyl-2-amino-n-butyric acid, cacodylic acid, beta-chlortriethylammonium-n-butyric acid, codeine, cyclohexylamine, cystine, n-decylamine, diethylamine, n-dodecaneamine, 1-ephedrine, 1-amino-3-methoxyethane, 1,2-bismethylaminoethane, 2-aminoethanol, ethylenediamine, ethylenediaminetetraacetic acid, 1-glutamic acid, alpha-monoethylglutamic acid, 1-glutamine, 1-glutathione, glycine, n-acetylglycine, dimethylglycine, glycylglycylglycine, leucylglycine, methylglycine, phenylglycine, N-n-propylglycine, tetraglycylglycine, glycylserine, dexadecaneamine, 1-aminoheptane, 2-aminoheptane, 2-aminohexanoic acid, DL-histidine, beta-alanylhistidine, imidazol, 1-aminoindane, 2-aminoisobutyric acid, isoquinoline, 1-aminoisoquinoline, 7-hydroxyisoquinoline, 1-leucine, glycylleucine, methionine, methylamine, morphine, morpholine, 1-amino-6-hydroxynaphthalene, dimethylaminonaphthalene, alpha-naphthylamine, beta-naphthylamine, n-methyl-alpha-naphthylamine, cis-neobornylamine, nicotine, n-nonylamine, octadecaneamine, octylamine, ornithine, papaverine, 3-aminopentane, valeric acid, permidine, phenanthridine, 1,10-phenanthroline, 2-ethoxyaniline, 3-ethoxyaniline, 4-ethoxyaniline, alpha-picoline, beta-picoline, gamma-picoline, pilocarpine, piperazine, trans-2,5-dimethylpiperazine, 1-n-butylpiperidine, 1,2-dimethylpiperidine, 1-ethylpiperidine, 1-methylpiperidine, proline, hydroxyproline, 1-amino-2,2dimethylpropane, 1,2-diaminopropane, 1,3-diaminopropane, 1,2,3-triaminopropane, 3-aminopropanoic acid, pteridine, 2-amino4,6-dihydroxypteridine, 2-amino4-hydroxypteridine, 6-chloropteridine, 6-hydroxy4-methylpteridine, purine, 6-aminopurine, 2-dimethylaminopurine, 8-hydroxypurine, 2-methylpyrazine, 2-amino-4,6-dimethylpyrimidine, pyridine, 2-aldoximepyridine, 2-aminopyridine, 4-aminopyridine, 2-benzylpyridine, 2,5-diaminopyridine, 2,3-dimethylpyridine, 2,4-dimethylpyridine, 3,5-dimethylpyridine, 2-ethylpyridine, methyoxypyridine, 4-methylaminopyridine, 2,4,6-trimethylpyridine, 1,2-dimethylpyrrolidine, n-methylpyrrolidine, 5-hydroxyquinazoline, quinine, 3-quinolinol, 8-quinolinol, 8-hydroxy-5-sulfoquinoline, 6-methoxyquinoline, 2-methylquinoline, 4-methylquinoline, 5-methylquinoline, serine, strychnine, taurine, myristilamine, 2-aminothiazole, threonine, o-toluidine, m-toluidine, p-toluidine, 2,4,6-triamino-1,2,3-triazine, tridecaneamine, trimethylamine, tryptophan, tyrosine, tyrosineamide, valine, salts thereof, and mixtures thereof.

Other suitable buffering agents can be, for example, acetic acid, acetoacetic acid, acrylic acid, adipamic acid, adipic acid, d-alinine, allantoin acid, alloxanic acid, alpha-aminoacetic acid, o-aminobenzoic acid, p-aminobenzoic acid, m-aminobenzosulfonic acid, p-aminobenzosulfonic acid, anisic acid, o-beta-anisylpropionic acid, m-beta-propionic acid, p-beta-propionic acid, ascorbic acid, DL-aspartic acid, barbituric acid, benzoic acid, m-bromobenzoic acid, n-butyric acid, iso-butyric acid, cacodylic acid, n-caproic acid, iso-caproic acid, m-chlorobenzoic acid, p-chlorobenzoic acid, beta-chlorobutyric acid, gamma-chlorobutyric acid, o-chlorocinnamic acid, m-chlorocinnamic acid, p-chlorocinnamic acid, o-chlorophenylacetic acid, m-chlorophenylacetic acid, p-chlorophenylacetic acid, beta-(o-chlorophenyl) propionic acid, beta-(m-chlorophenyl)propionic acid, beta-(p-chlorophenyl)propionic acid, beta-chloropropionic acid, cis-cinnamic acid, trans-cinnamic acid, o-cresol, m-cresol, p-cresol, trans-crotonic acid, cyclohexane-1:1-dicarboxylic acid, cyclopropane-1:1-dicarboxylic acid, DL-cysteine, L-cysteine, deuteroacetic acid, 2,3-dichlorophenol, 3,4-dihydroxybenzoic acid, 3,5-dihydroxybenzoic acid, dimethylglycine, dimethylmalic acid, 2,4-dintirophenol, 3,6-dinitrophenol, diphenylacetic acid, ethylbenzoic acid, formic acid, trans-fumaric acid, gallic acid, glutaramic acid, glutaric acid, glycine, glycolic acid, heptanoic acid, hexahydrobenzoic acid, hexanoic acid, hippuric acid, histidine, hydroquinone, m-hydroxybenzoic acid, p-hyroxybenzoic acid, beta-hyroxybutyric acid, gamma-hydroxybutyric acid, beta-hydroxypropionic acid, gamma-hydroxyquinoline, iodoacetic acid, m-iodobenzoic acid, itaconic acid, lysine, maleic acid, malic acid, malonic acid, DL-mandelic acid, mesaconic acid, mesitylenic acid, methyl-o-aminobenzoic acid, methyl-m-aminobenzoic acid, methyl-p-aminobenzoic acid, o-methylcinnamic acid, m-methylcinnamic acid, p-methylcinnamic acid, beta-methylglutaric acid, n-methylglycine, methylsuccinic acid, o-monochlorophenol, m-monochlorophenol, p-monochlorophenol, alpha-naphthoic acid, beta-naphthoic acid, alpha-naphthol, beta-naphthol, nitrobenzene, m-nitrobenzoic acid, p-nitrobenzoic acid, o-nitrophenol, m-nitrophenol, p-nitrophenol, o-nitrophenylacetic acid, m-nitrophenylacetic acid, p-nitrophenylacetic acid, o-beta-nitrophenylpropionic acid, m-beta-nitrophenylpropionic acid, p-beta-nitrophenylpropionic acid, nonanic acid, octanoic acid, oxalic acid, phenol, phenylacetic acid, o-phenylbenzoic acid, gamma-phenylbutyric acid, alpha-phenylpropionic acid, beta-phenylpropionic acid, o-phthalic, m-phthalic, p-phthalic, pimelic acid, propionic acid, isopropylbenzoic acid, 2-pyridinecarboxylic acid, 3-pyridinecarboxylic acid, 4-pyridinecarboxylic acid, pyrocatecchol, resorcinol, saccharin, suberic acid, succinic acid, alpha-tartaric acid, meso-tartaric acid, theobromine, terephthalic acid, thioacetic acid, thiophenecarboxylic acid, o-toluic acid, m-toluic acid, p-toluic acid, trichlorophenol, trimethylacetic acid, tryptophan, tyrosine, uric acid, n-valeric, iso-valeric, veronal acid, vinylacetic acid, xanthine, salts thereof, and mixtures thereof.

Further suitable buffering agents can be, for example, arsenic acid, arsenious acid, o-boric acid, carbonic acid, chromic acid, germanic acid, hyrocyanic acid, hydrofluoric acid, hydrogen sulfide, hypobromous acid, nitrous acid, o-phosphoric acid, phosphorous acid, pyrophosphoric acid, selenious acid, m-silicic acid, o-silicic acid, sulfurous acid, telluric acid, tellureous acid, tetraboric acid, salts thereof, and mixtures thereof.

Buffering agents in the present compositions can be, for example, 3-chloropropanoic acid, citric acid, ethylenedinitrilotetraacetic acid (i.e., "EDTA"), alanine, aminobenzene, sulfanilic acid, 2-aminobenzoic acid, 2-aminophenol, ammonia, arginine, asparagine, aspartic acid, dimethyleneimine, benzene-1,2,3-tricarboxylic acid, benzoic acid, benzylamine, 2,2-bipyridine, butanoic acid, maleic acid, carbonic acid, dichloroacetic acid, diethylamine, catechol, resorcinol, d-tartaric acid, ethylenediamine, glutamic acid, glutamine, glycine, adipic acid, hydrogen hypophosphite, isoleucine, leucine, methionine, 3-nitrobenzoic acid, 4-nitrobenzoic acid, phthalic acid, iodoacetic acid, histidine, lysine, 4-methylaniline, ocresol, 2-naphthoic acid, nitrilotriacetic acid, 2-nitrobenzoic acid, 4-nitrophenol, 2,4-dinitrophenol, N-nitrosophenylhydroxylamine, nitrous acid, phosphoric acid, phenylalanine, piperdine, serine, hydrogen sulfite, threonine, tris(hydroxymethyl)aminomethane (i.e. "TRIS" or "THAM"), tyrosine; alkali metal salts thereof; and mixtures thereof. Still further suitable buffering agents can be, for example, zwitterionic buffers, such as MES, lysine, bisine, and like compounds, salts thereof, or mixtures thereof. Still further suitable buffering agents can be, for example, the so-called "Goode" buffers generally and which buffers may encompass some of the abovementioned buffers or compounds and which buffers are typically and advantageously biologically inert and do not interfere with biochemical reactions.

Surfactants

The buffer compositions of the present disclosure can optionally include one or more surfactant or a co-surfactant. The surfactant or co-surfactant can be nonionic surfactants, anionic surfactants, zwitterionic surfactants such as lauryl sarcosine, fluorocarbon surfactants (which are differentiated from the fluorocarbon superwetting agents of the present disclosure by, for example, having other structures, other surface activities, or both), and like surfactants, or mixtures thereof. An excellent source listing of surfactant materials is provided by McCutcheon's Vol. 1: *Emulsifiers and Detergents*, North American Ed., McCutheon Division, MC Publishing Co., 1995, the disclosure of which is incorporated herein by reference. Suitable nonionic surfactants include, but are not limited to, alkyl ethoxylated surfactants, block copolymer surfactants, castor oil surfactants, sorbitan ester surfactants, polyethoxylated fatty alcohol surfactants, glycerol mono-fatty acid ester surfactants, polyethylene glycol fatty acid ester surfactants, and mixtures thereof. Other useful nonionic alkyl alkoxylated surfactants are ethoxylated alkyl amines derived from the condensation of ethylene oxide with hydrophobic alkyl amines. Other examples of useful ethoxylated surfactants include carboxylated alcohol ethoxylate, also known as ether carboxylate.

Anionic surfactants can optionally be incorporated in the present compositions as a surfactant or co-surfactant. Many suitable non-limiting examples from the class of anionic surfactants can be found in McCutcheon's (supra) as well as *Surfactants and Interfacial Phenomena*, 2nd Ed., Milton J. Rosen, 1989, John Wiley & Sons, Inc., pp. 7-16, which is hereby incorporated by reference. Additional suitable non-limiting examples of anionic surfactants can be found in *Handbook of Surfactants*, M. R. Porter, 1991, Blackie & Son Ltd, pp. 54-115 and references therein, the disclosure of which is incorporated herein by reference.

Hybridization

Other components such as water may also be added to form a diluted mixture of the buffer. A second oligonucleotide material can be added to the buffer concentrate or to the diluted mixture. The resulting buffer mixture, alone or in combination with a second oligonucleotide material is placed into an array. The second oligonucleotide material can be the same as the first oligonucleotide material affixed to the array, different from the first oligonucleotide material, or combinations or mixtures thereof. The compositions of the present disclosure are generally prepared by mixing one or more the listed ingredients to form a buffer concentrate solution. The buffer concentrate can be conveniently diluted to desired use concentrations.

There are numerous types of substrates used in hybridization assays. Common substrates or supports used for array assays are surface-modified siliceous substrates, such as glass. DNA microarrays are typically, but not always, synthesized or deposited onto these substrates. The substrate surface is modified to enable or facilitate the initial attachment of nucleic acids to the surface for the manufacture of the array probes. Surface modification or derivatization techniques are known in the art. A common surface derivatization is silane-based.

Arrays of oligomer probes, such as oligonucleotides or polynucleotides, are hybridized using conventional methods and hybridization solutions. J. Sambrook, E. F. Fritsch, T. Maniatis, *Molecular Cloning: A Laboratory Manual*, Cold Spring Harbor Laboratory Press, Cold Spring Harbor, 2nd Ed., 1989, vol. 1-3, incorporated herein by reference, describe the considerations and conditions for hybridization of oligonucleotide probes. Probe length, hybridization temperature, as well as other factors well known in the art affect hybridization conditions. Typically, hybridizations using synthetic oligomers are usually carried out under conditions that are 5-10° C. below the calculated melting temperature $T_m$ of a perfect hybrid to minimize mismatched or non-Watson/Crick base pairing between the probe and target, and maximize the rate at which Watson/Crick base pairs form. Other factors influencing the rate of hybrid formation include the salt concentration, the presence of solvents or co-solvents, the concentration of nucleic acid in solution, the length of hybridization, and the degree and method of agitation.

A conventional hybridization solution can typically comprise, for example, a salt (e.g. a monovalent cation), a buffer that provides buffering capacity between pH 6.8-8.5 (more typically between pH 7.0-7.5), a divalent cation chelating agent (e.g., ethylenediaminetetraacetic acid, EDTA), and agents for blocking non-specific binding of targets to the array surface, such as surfactants, proteins, a carrier DNA from an organism unrelated to the experiment at hand, and like ingredients. A typical hybridization solution contains 6× SSPE (0.9 M NaCl, 60 mM sodium phosphate (pH 7.4); 6 mM EDTA); or 6×SSC (0.9 M NaCl, 90 mM sodium citrate (pH 7.0)), 0.5% w/v sodium dodecyl sulfate (SDS); 100 micrograms/mL denatured, fragmented salmon sperm DNA; and 0.1% w/v nonfat dried milk. Conventional hybridization solutions and methods can be improved by modifying them in accordance with the method and composition of the present disclosure.

An array can be hybridized according to standard protocols as disclosed or referenced herein for a period of time ranging from about 2 hours to about 2 days, depending on at least the make-up of the probes (i.e., probe length and diversity of probe composition) and the complexity of the target, for example, at a controlled temperature, which typically ranges from 20° C. to 70° C., depending on the melting temperature $T_m$, as discussed above. Low temperature hybridizations are performed at about 20° C. to about 50° C. (typically about 37-45° C.). High temperature hybridizations are performed at or around 55° C. to about 70° C. (typically 60° C. to 65° C.). However, for most nucleic acid microarrays, high temperature hybridizations are preferred in the art since the higher temperature maximizes the rate of Watson/Crick base pairing of nucleotides. The typical time period for hybridization of an array is overnight or longer (i.e., anywhere from 8 hours to at least 24 hours) so as to hybridize the target. The array is then washed and dried and optically scanned to measure the degree of hybridization using conventional methods and equipment that are known in the art. The aforementioned non-aqueous carriers, such as formamide, can be applicable here, particularly for example, for hybridizations accomplished at lower temperatures.

A typical microarray hybridization chamber has, for example, a thickness of about 0.4 mm, and contains about 0.5 mL of hybridization solution. As the thickness of the chamber is decreased, the volume of the hybridization solution needed to fill it also decreases, which can be advantageous for the user. However, as the thickness decreases, it becomes more difficult for the bubble to move around in the chamber, and it becomes more likely that bubble artifacts will be observed. This effect currently limits the thickness of the microarray hybridization chamber to about 0.4 mm.

It is sometimes advantageous to decrease the area of a hybridization chamber. As the area of a microarray hybridization chamber decreases, even if the thickness remains the same, the smaller bubble size that is required in the smaller chamber can be difficult to move reliably. This can cause anomalous sticking or mixing behavior, causing artifacts in the assay results.

In addition, the speed of the rotation can have an affect on the hybridization. At some speeds the bubble has a tendency to break up into multiple smaller bubbles, which can in turn exhibit anomalous sticking or mixing behavior, causing artifacts in the results. At other speeds, the bubble does not rotate around the perimeter of the slide uniformly or it does not rotate at all, which can cause artifacts in the results.

Standard Hybridization Protocol

As an example of a standard hybridization protocol, a series of control array comparative genomic hybridizations (aCGH) experiments that measured the copy number difference of X chromosome probes in male (XY) versus female (XX) hybridizations were accomplished according to a published protocol (Barrett et al., *Proc. Nat. Acad. Sci., USA*, 101:51, 17765-17770, (2004)) with minor modifications. Purified restricted DNA (6 micrograms) was labeled with a Bioprime labeling kit (Invitrogen) according to the manufacturer's directions in a 50 microliter volume with a modified dNTP pool; 120 microM each of dATP, dGTP, dCTP, 60 microM dTTP, and 60 microM of either Cy5-dUTP for the XY or Cy3-dUTP for the 46, XX female sample (Perkin-Elmer, Boston, Mass.). Labeled targets were subsequently filtered using a Centricon YM-30 filter (Millipore, Bedford, Mass.). Experimental and reference targets for each hybridization were pooled, mixed with 50 micrograms of human Cot-1 DNA (Invitrogen), 100 micrograms of yeast tRNA (Invitrogen) and 1× hybridization control targets (Agilent Technologies). The target mixture was purified then concentrated with a Centricon YM-30 column, and resuspended to a final volume of 250 microliters in the presence or absence of the superwetting agent, such as TEGO® Wet 260, then mixed with an equal volume of Agilent 2× in situ Hybridization Buffer. Alternatively, the TEGO® Wet 260 can be present in the 2× hybridization buffer. In either combination or mixing alternative, there is obtained a final concentration of TEGO® Wet 260 in the use composition of 1.5 weight % per volume based on the total volume (w/v).

Prior to hybridizing the array, the hybridization mixtures were denatured at 100° C. for 1.5 minutes and incubated at 37° C. for 30 minutes. The sample was applied to the array using an Agilent microarray hybridization chamber and hybridization was carried out for 14-18 hrs at 65° C. in a Robbins Scientific rotating oven at about 4-5 rpm. The arrays were then disassembled in 0.5×SSC/0.005% (w/v) Triton X-102 (wash 1) at 65° C. then washed for 5 minutes at room temperature in wash 1, followed by 5 minutes at 37° C. in 0.1×SSC/0.005% (w/v) Triton X-102 (wash 2). Slides were dried and scanned using an Agilent 2565AA DNA microarray scanner.

The distributions (plots not shown) of the $\log_2$ ratios for the X chromosome probes for the XY/XX comparisons had a median value of −0.8 to −0.95 in repeat experiments consistent with the one copy of X chromosome in the XY (Cy5) samples versus the two copies in the XX (Cy3) samples. In contrast the distributions of the autosome probes, representing chromosomes 1-22 in the same experiments were centered on 0 consistent with the equal copy numbers in each sample.

Examples 2, and 5 through 7 described below were performed under the same or similar conditions to the above-mentioned standard protocol, with the exception that a slower rotation rate (3 rpm) for the low volume hybridizations can be used. In addition, after the arrays are warmed in the oven for 30 minutes, they can be removed briefly and any multiple bubbles present can be consolidated by gently tapping the array or the array holder.

A number of different protocols have been reported for effecting mixing during hybridization of DNA microarrays. These include, for example, the procedures described for the use of the Agilent microarrays, the Affymetrix GeneChip®, the Amersham Codelink® Biochip, and the BioMicro MAUI® Hybridization System. Substrate wetting, fluid mixing, or both, can be important considerations in many DNA hybridization techniques. The methods and compositions of the present disclosure can provide improved wetting and mixing in many different protocols to provide an alternative hybridization technique.

The methods and composition of the present disclosure need not limited to uses in DNA hybridization. Systems that are designed for the analysis of proteins or small molecules, such as protein or peptide arrays, encounter many of the same substrate wetting and fluid mixing problems as in DNA hybridization, and can benefit from the use of superwetting agents of the present disclosure. Other systems, such as microfluidic based assays, in which it is desirable for fluids to be transported through narrow channels or capillaries, can also benefit from the use of superwetting agents.

EXAMPLES

The following examples serve to more fully describe the manner of using the above-described disclosure, as well as to set forth the best modes contemplated for carrying out various aspects of the disclosure. It is understood that these examples in no way serve to limit the true scope of this disclosure, but rather are presented for illustrative purposes. The percentages used in the Examples are by weight per weight (w/w), and the solutions are expressed as weight per volume (w/v).

Example 1

A hybridization buffer concentrate (2×) composition is prepared by mixing: 1,225 mM LiCl, 300 mM lithium 2-[N-morpholino] ethane sulfonic acid (Li-MES) of pH of 6.1, 12 mM EDTA chelator, 3% (w/v) lithium dodecyl sulfate (LiDS), 2% (w/v) Triton X-100 non-ionic surfactant, and 3% (w/v) TEGO® Wet 260 superwetting agent. The buffer concentrate (2×) composition is summarized in the accompanying table.

A 2× Hybridization Buffer Concentrate

| Final Concentration | Component | Volume (microliters) |
|---|---|---|
| | Nuclease-free water | 1,730 |
| 1,225 mM | 8.0 M LiCl | 1,530 |
| 300 mM | 1.0 M Li-MES (pH 6.1) | 3,000 |
| 12 mM | 0.5 M EDTA (pH 8.0) | 240 |
| 3.0% (w/v); | 15% Lithium Dodecyl Sulfate; | 2,000 |
| 2.0% (w/v) | 10% Triton X-100 | |
| 3.0% (w/v) | 20% TEGO ® Wet 260 | 1,500 |
| Total monovalent cation is 1,500 mM | Volume 2X (mL) | 10 |

Example 2

A target solution is prepared according to standard protocols, and diluted with 1 part of the 2× buffer, to yield a 1× buffer having 1.5% (w/v) TEGO® Wet 260 superwetting agent content. Hybridization and washes were performed according to the example standard protocol.

Example 3

Referring to the Figures, FIG. 1 shows a comparative scatter plot of feature intensity for two arrays, with and without scar defects. The data point cluster(s) of features that appear off-axis can be attributed to bubble scar defects (photo not shown) in the comparative array prepared without a superwetting agent present. The array prepared with a superwetting agent present was free of bubble scar defects (photo not shown). The data points appearing substantially on a single line with a slope of one are attributed to similar feature intensities on the comparative arrays.

Example 4

Addition of LIDS to prevent phase separation. A series of solutions were prepared containing a range of concentrations of both TEGO® Wet 260 and lithium dodecyl sulfate (LiDS) in buffer containing 612 mM LiCl, 150 mM Li-MES pH 6.1, 6 mM EDTA and 1% (w/v) Triton X-100. TEGO® Wet 260 concentrations ranged from 0 to 8% (w/v), and LiDS concentrations ranged from 0 to 4% (w/v). All of the preparations were apparently homogeneous solutions at room temperature. In the absence of TEGO® Wet 260, all of the solutions remained a single-phase when heated to 65° C. When TEGO® Wet 260 was included in the preparations some of the single-phase preparations produced a second phase, i.e., separated out into two phases, when heated at 65° C. The separated second phase consisted largely of TEGO® Wet 260. The presence of LiDS in sufficient or excess amounts stabilized the system such that phase separation was not observed. The amount of LiDS needed to maintain a single phase and prevent phase separation was dependent on the amount of TEGO® Wet 260 present as summarized in the accompanying table. The results were used to prepare a phase diagram (not shown).

| TEGO ® Wet 260 w/v % | LiDS w/v % for single phase at 65° C. |
|---|---|
| 0.125 | 0.125 |
| 0.25 | 0.5 |
| 0.5 | 0.5 |
| 1.0 | 1.0 |
| 2.0 | 1.0 |
| 4 | 2.0 |

Example 5

Comparison of small volume, higher concentration of target hybridization, to large volume hybridization. Two array Comparative Genomic Hybridizations (array CGH) were performed, one with larger volume having a 450 microliter sample volume in a 400 micron thick chamber (total volume of the chamber about 530 microliters), and one with a smaller volume having a 175 microliter sample volume in a 175 micron thick chamber (total volume of the chamber about 230 microliters). Equal amounts of DNA target were present in both hybridizations. The signal intensities resulting from the smaller volume hybridization were about 3 times greater than those observed in the larger volume hybridization. The level of background signal observed was the approximately the same in both cases. The standard deviation of the $Log_2$ Ratios was lower in the case of the smaller volume hybridization. The results were used to prepare a comparative plot of standard deviations (not shown).

Example 6

Comparison of small volume, lower amount of target hybridization, to large volume hybridization. Two array CGH experiments were performed, one large volume hybridization with 6 micrograms of genomic material in 475 microliter sample volume in a 400 micron thick chamber (total volume of the chamber about 530 microliters), and one small volume with 1 microgram genomic material in 125 microliter sample volume in a 110 micron thick chamber (total volume of the chamber about 145 microliters). The signal intensities and background for both hybridizations were approximately the same. According to the plotted results (not shown) both the small and large hybridizations showed approximately the same $Log_2$ ratio separation of about 0.85, with similar standard deviations.

Example 7

Comparison of hybridizations with slow rotation with and without TEGO Wet 260, to hybridizations with fast rotation (20 rpm) with TEGO Wet 260. Multiple Array CGH were performed, all using a 475 microliter sample volume in a 400 micron thick chamber (total volume of the chamber about 530 microliters). Six hybridizations were performed at 5 rpm (slow) without TEGO® Wet 260. Three hybridizations were performed at 5 rpm (slow) with 1.5% (w/v) TEGO® Wet 260 added. Three hybridizations were performed at 20 rpm (faster) with 1.5% (w/v) TEGO® Wet 260 added. Equal amounts and concentrations of DNA target were present in all hybridizations. The signal levels for the hybridizations done at 20 rpm were approximately twice that of the signal levels observed for the hybridizations done at 5 rpm. The signal-to-noise ratios for the hybridizations performed with TEGO® Wet 260 at 20 rpm were consistently higher than those observed for the 5 rpm hybridizations done with or without TEGO® Wet 260. According to the plotted results (not shown) the standard deviations of the $Log_2$ Ratios were lower for the hybridizations performed in the presence of TEGO® Wet 260, at both 5 rpm and 20 rpm.

The entire disclosure for publications, patents, and patent documents are incorporated herein by reference, as though individually incorporated by reference. The disclosure has been described with reference to various specific embodiments and techniques. Additional aspects of the disclosure are additionally described and illustrated in the FIGURE(S) provided, if any. However, it should be understood that many variations and modifications are possible while remaining within the spirit and scope of the disclosure.

The claimed invention is:

1. A method of hybridizing comprising:
   contacting a first oligonucleotide bound to a silaceous surface with a second unbound oligonucleotide in the presence of an aqueous mixture comprising a superwetting agent,
   wherein said contacting is done under conditions that provide for hybridization of the first oligonucleotide with the second oligonucleotide, and
   wherein the contacting is done in the presence of a moving gas bubble that dispels the aqueous mixture across said silaceous surface.

2. The method according to claim 1 wherein the superwetting agent comprises an organosilicone wetting agent, an organofluorine wetting agent, a hydrocarbyl wetting agent, or mixtures thereof.

3. The method according to claim 2 wherein the superwetting agent is a polyether siloxane copolymer.

4. The method according to claim 2 wherein the superwetting agent is an organofluorine compound selected from the group consisting of compounds of the formulas:

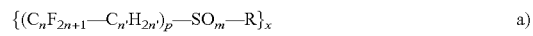

$\{(C_nF_{2n+1}-C_{n'}H_{2n'})_p-SO_m-R\}_x$        a)

wherein m is from 1 to 3; n is from about 3 to about 20; n' is from about 0 to about 20; p is from 1 to 2; x is from about 1 to about 100; R is hydrogen, $(C_{1-10})$ saturated alkyl, or $(C_{2-10})$ unsaturated alkyl; or salts thereof;

$(C_nF_{2n+1}-C_{n'}H_{2n'})_p-R^1$        b)

wherein
$R^1$ is monovalent or divalent radical selected from
—H,
halo,
—OH,
$(C_{1-10})$ alkyl, ($C_{2-10}$) unsaturated alkyl,
—$CH_2$—O—C(=O)—($C_{1-20}$) alkyl
—$CH_2$—O—C(=O)—($C_{2-20}$) unsaturated alkyl
—O—P(=O)(OH)$_2$,
—O—P(=O)(—OH)—,
—O—P(=O)(OH)(—O—$CH_2$—$CH_2$—)$_o$—OH,
—$CO_2H$,
—$^{(+)}N(R^2)^2$—$O^{(-)}$,
—$^{(+)}N(R^2)^2$—$CH_2$—$CO_2H$,
—O—C(=O)—$CH_2$—CH($SO_3H$)—C(=O)—O—,
—O($CH_2$—$CH_2$—O)y—H,
—S—$CH_2$—$CH_2$—C(=O)—OH, and
($C_{1-10}$)alkyl-C(=O)—O—CH—$CH_2$—$^{(+)}N(R^2)_2$—(—$CH_2$)$_{1-4}$—$CO_2H$, each $R^2$ is independently hydrogen, or ($C_{1-10}$) alkyl,
m is from 1 to 2;
n is from about 1 to about 20;
n' is from about 1 to about 20;
o is from about 1 to about 10;
p is from 1 to 2; and
y is from 0 to about 20;
or salts thereof;

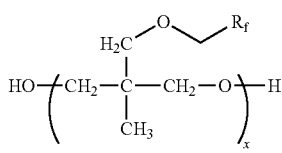

c)

wherein $R_f$ is a monovalent perfluorinated radical of the formula —$C_nF_{2n+1}$;
n is from about 1 to about 20; and
x is from 1 to 100;
or salts thereof;
and mixtures thereof.

5. The method according to claim 2 wherein the hydrocarbyl wetting agent is an alkoxylated hydrocarbyl compound of the formula:

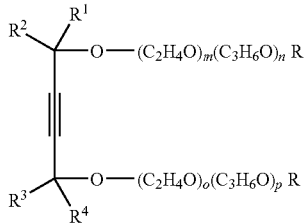

wherein
R is hydrogen or an alkyl radical having from 1 to 4 carbon atoms,
$R^1$ to $R^4$ are each independently hydrogen or an alkyl radical having from 3 to 10 carbon atoms, and
m, n, o and p are from 0 to 30 and a sum of 3 to about 60, inclusive.

6. The method according to claim 1 wherein the buffer capacity and the pH of the aqueous mixture is at from about 5 to about 9.

7. The method according to claim 1 wherein contacting is accomplished at a temperature of from about 30° C. to about 70° C.

8. The method according to claim 1 wherein the aqueous mixture further comprises at least one of:
an organosulfonic acid;
an organosulfate surfactant;
an organopolyalkoxylate;
a source of a monovalent cation;
a chelator; or
mixtures thereof.

9. The method according to claim 1 wherein the aqueous mixture further comprises a second oligonucleotide material.

10. The method according to claim 1 further comprising a second contacting of the surface with an aqueous mixture comprising a superwetting agent and a second oligonucleotide material.

11. The method according to claim 1 wherein the surface is a silane surface-modified siliceous microarray.

12. The method of claim 1, wherein the aqueous mixture is a buffer comprising an organic compound, an inorganic compound, or mixtures thereof.

13. The method of claim 12, wherein the buffer comprises one or more of
a source of a monovalent cation;
a water soluble organosulfonic acid or salt thereof;
a chelator or salt thereof;
an organosulfonic surfactant or salt thereof;
an organopolyalkoxylate; and
an aqueous carrier.

14. The method of claim 13, wherein
the source of a monovalent cation is an alkali metal halide salt;
the organosulfonic acid is a morpholino-substituted alkyl sulfonic acid;
the chelator is a divalent cation chelating agent;
the organosulfate surfactant is a ($C_8$-$C_{16}$)alkyl sulfate;
the organopolyalkoxylate is an alkoxylated alkylphenol;
the superwetting agent is a polyether siloxane copolymer; and
the aqueous carrier is water.

15. The method of claim 13, wherein
the superwetting agent is present in the buffer from about 0.05 to about 50 weight percent of the total buffer;
the water soluble organosulfonic acid is present in the buffer from about 0.01 to about 10 weight percent of the total buffer;
the organosulfate surfactant is present in the buffer from about 0.1 to about 50 weight percent of the total buffer;
the organopolyalkoxylate is present in the buffer from about 0.1 to about 50 weight of the total buffer;
the chelator is present in the buffer from about 0.01 to about 10 weight percent of the total buffer; and
the source of a monovalent cation is present in the buffer from about 0.01 to about 50 weight percent of the total buffer.

16. The method of claim 2, wherein the superwetting agent is selected from the group consisting of:
an organosilicone compound of the formula

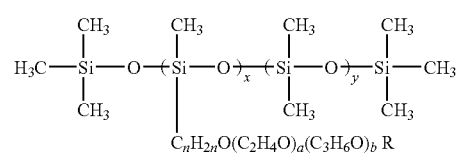

wherein x is from about 1 to about 10; y is from about 0 to about 10; n is from about 3 to about 4; a is from about 0 to about 15; b is from about 0 to about 14; such that at least one of a and b is not zero and a+b is from about 1 to about 30; and R is selected from the group consisting of hydrogen, an alkyl group having from about 1 to about 4 carbon atoms, an acetyl group;

an organofluorine compound selected from the group consisting of a compound of the formulas:

$$\{(C_nF_{2n+1}-C_{n'}H_{2n'})_p-SO_m-R\}_x \qquad a)$$

wherein m is from 1 to 3; n is from about 3 to about 20; n' is from about 0 to about 20; p is from 1 to 2; x is from about 1 to about 100; R is hydrogen, $(C_{1-20})$ saturated alkyl, or $(C_{2-20})$ unsaturated alkyl; or salts thereof;

$$(C_nF_{2n+1}-C_{n'}H_{2n'}')_p-R^1 \qquad b)$$

wherein
$R^1$ is monovalent or divalent radical selected from
—H,
halo,
—OH,
$(C_{1-10})$ alkyl,
$(C_{2-10})$ unsaturated alkyl,
—$CH_2$—O—C(=O)—$(C_{1-20})$ alkyl
—$CH_2$—O—C(=O)—$(C_{2-20})$ unsaturated alkyl
—O—P(=O)(OH)$_2$,
—O—P(=O)(—OH)—,
—O—P(=O)(OH)(—O—$CH_2$—$CH_2$—)$_o$—OH,
—$CO_2$H,
—$^{(+)}N(R^2)^2$—O$^{(-)}$,
—$^{(+)}N(R^2)^2$—$CH_2$—$CO_2$H,
—O—C(=O)—$CH_2$—CH(SO$_3$H)—C(=O)—O—,
—O(CH$_2$—CH$_2$—O)y—H,
—S—CH$_2$—CH$_2$—C(=O)—OH, and
$(C_{1-10})$alkyl-C(=O)—O—CH—CH$_2$—$^{(+)}$N(R$^2$)$_2$—(—CH$_2$)$_{1-4}$—CO$_2$H,
wherein each $R^2$ is independently hydrogen, or $(C_{1-10})$ alkyl,
m is from 1 to 2;
n is from about 1 to about 20;
n' is from about 1 to about 20;
o is from about 1 to about 10;
p is from 1 to 2; and
y is from 0 to about 20;

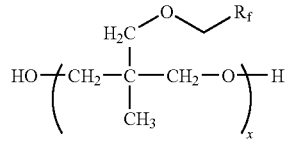

wherein
$R_f$ is monovalent radical of the formula —$C_nF_{2n+1}$;
n is from about 1 to about 20; and
x is from 1 to 100;
or salts thereof;
an alkoxylated hydrocarbyl compound of formula:

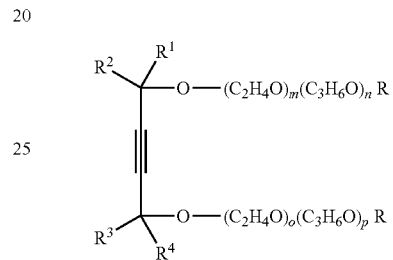

wherein
R is hydrogen or an alkyl radical having from 1 to 4 carbon atoms,
$R^1$ to $R^4$ are each hydrogen or an alkyl radical having from 3 to 10 carbon atoms,
m, n, o and p are from 0 to 30 and a sum in the range of 3 to 60, inclusive;
and mixtures thereof.

* * * * *

UNITED STATES PATENT AND TRADEMARK OFFICE
CERTIFICATE OF CORRECTION

| | | |
|---|---|---|
| PATENT NO. | : 7,618,777 B2 | Page 1 of 1 |
| APPLICATION NO. | : 11/082476 | |
| DATED | : November 17, 2009 | |
| INVENTOR(S) | : Joel Myerson et al. | |

It is certified that error appears in the above-identified patent and that said Letters Patent is hereby corrected as shown below:

In column 28, line 35, in Claim 1, delete "silaceous" and insert -- siliceous --, therefor.

In column 28, line 44, in Claim 1, delete "silaceous" and insert -- siliceous --, therefor.

In column 29, line 2, in Claim 4, delete "alkyl" and insert -- alkyl, --, therefor.

In column 29, line 3, in Claim 4, delete "alkyl" and insert -- alkyl, --, therefor.

In column 31, line 13, in Claim 16, delete "(C2-20)" and insert -- (C2-10) --, therefor.

In column 31, line 22, in Claim 16, delete "alkyl" and insert -- alkyl, --, therefor.

In column 31, line 23, in Claim 16, delete "alkyl" and insert -- alkyl, --, therefor.

Signed and Sealed this

Second Day of February, 2010

David J. Kappos
*Director of the United States Patent and Trademark Office*